United States Patent
Skelton

(10) Patent No.: US 9,566,441 B2
(45) Date of Patent: Feb. 14, 2017

(54) DETECTING POSTURE SENSOR SIGNAL SHIFT OR DRIFT IN MEDICAL DEVICES

(75) Inventor: Dennis M. Skelton, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 1718 days.

(21) Appl. No.: 12/771,854

(22) Filed: Apr. 30, 2010

(65) Prior Publication Data

US 2011/0270134 A1 Nov. 3, 2011

(51) Int. Cl.
*A61B 5/11* (2006.01)
*A61N 1/365* (2006.01)

(52) U.S. Cl.
CPC ... *A61N 1/36514* (2013.01); *A61B 2562/0219* (2013.01); *A61N 1/36535* (2013.01)

(58) Field of Classification Search
USPC ........... 600/300–301, 587, 594–595; 606/62; 607/1–2, 43, 48, 49, 62–63, 115
See application file for complete search history.

(56) References Cited

U.S. PATENT DOCUMENTS

| | | |
|---|---|---|
| 4,297,685 A | 10/1981 | Brainard, II |
| 4,365,633 A | 12/1982 | Loughman |
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from nonlinear mathematics: Clinical applicability and prognostic significance," http://herkules.oulu.fi.isbn9514250133/html, 4 pp., 2004.

(Continued)

*Primary Examiner* — Deborah Malamud
(74) *Attorney, Agent, or Firm* — Shumaker & Sieffert, P.A.

(57) ABSTRACT

In general, the disclosure relates to medical devices and systems for detecting the posture state of patient. For example, a medical system may detect a posture state of a patient and deliver therapy based at least in part on the detected patient posture state. In some examples, the system may comprise a posture sensor that generates posture sensor data when a patient is in a posture state, and a processor that receives the first posture sensor data, compares the first posture state data to reference posture sensor data, and detects the presence of at least one of sensor signal drift or sensor signal shift for the posture sensor based at least in part on the comparison. In some examples, the processor may be configured to determine one or more offset correction values to apply to posture sensor data generated by the posture sensor when the at least one of sensor signal drift or sensor signal shift is determined to be present.

34 Claims, 20 Drawing Sheets

(56) References Cited

U.S. PATENT DOCUMENTS

| | | |
|---|---|---|
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |

(56) References Cited

U.S. PATENT DOCUMENTS

| | | |
|---|---|---|
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0192038 A1* | 8/2007 | Kameyama ............... 702/19 |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |

(56) References Cited

U.S. PATENT DOCUMENTS

| | | |
|---|---|---|
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2008/0312553 A1* | 12/2008 | Timmons ............ 600/561 |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/87433 | 11/2002 |
| WO | 02/96512 | 12/2002 |
| WO | 02/100267 | 12/2002 |
| WO | 03/51356 | 6/2003 |
| WO | 03/65891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

(56) References Cited

OTHER PUBLICATIONS

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ce.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

\* cited by examiner

US 9,566,441 B2

DETECTING POSTURE SENSOR SIGNAL SHIFT OR DRIFT IN MEDICAL DEVICES

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to techniques for detecting signal shift and/or signal drift in the output of one or more postures sensors of a medical device. In some examples, the medical device may be an IMD that delivers electrical stimulation therapy to the patient. The IMD may detect the posture state of the patient via a posture state module and deliver medical therapy to the patient according to the detected posture state. For example, the IMD may automatically adjust one or more therapy parameter values or other characteristics of the therapy based on the detected posture state. To detect the posture state of a patient, a posture state module of an IMD or other medical device may include one or more posture sensors, such as, e.g., one or more accelerometers. The sensor output signal(s) generated by the one or more posture sensors of the posture state module may be indicative of patient posture state. For example, the posture state of a patient may be detected by comparing the sensor output signal(s) to posture state reference data that defines specific patient posture states.

In some examples, an offset signal shift and/or offset signal drift may be present in an output signal generated by the one or more posture sensors. An IMD or other medical device may detect the presence of the sensor signal offset shift and/or offset drift by comparing sensor data generated by a posture sensor to reference posture sensor data. Such a comparison may be performed for posture sensor data generated by the posture sensor when the patient occupies each of one or more posture states. In some examples, the reference posture sensor data is associated with one or more particular patient posture states. The reference posture sensor data may define sensor signal data, for example, for one or more particular posture states of the patient in which signal offset shift and/or drift is not substantially present or is present only in an insignificant and/or acceptable amount.

In some examples, upon detection of the offset shift and/or offset drift in the output of a posture sensor, the IMD or other medical device may determine and apply an offset correction to a posture state detection algorithm utilized to detect the posture state of the patient based on the output of the posture sensor. The applied offset correction may account for any inaccuracies in the detection of patient posture state that may result from the detected offset signal shift and/or offset drift. Additionally or alternatively, an IMD or other medical device may suspend delivery of therapy to a patient on a posture state responsive basis or otherwise prevent delivery of posture responsive therapy to the patient, e.g., by preventing activation of posture responsive therapy delivery mode, until the detected offset shift and/or drift in the output of the posture sensor is addressed.

In one example, the disclosure relates to a method comprising receiving posture sensor data from a posture sensor; comparing the posture sensor data from the posture sensor to reference posture sensor data; and detecting the presence of at least one of sensor signal drift or sensor signal shift for the posture sensor based at least in part on the comparison, wherein the posture sensor data is indicative of a posture state of a patient.

In another example, the disclosure relates to a medical device comprising a posture sensor configured to generate posture sensor data; and a processor configured to receive the posture sensor data, compare the posture sensor data to reference posture sensor data, and detect at least one of sensor signal drift or sensor signal shift for the posture sensor based at least in part on the comparison, wherein the posture sensor data is indicative of a posture state of a patient.

In another example, the disclosure relates to a computer-readable storage medium comprising instructions to cause one or more processors to receive posture sensor data from a posture sensor; compare the posture sensor data from the posture sensor to reference posture sensor data; and detect at least one of sensor signal drift or sensor signal shift for the posture sensor based at least in part on the comparison, wherein the posture sensor data is indicative of a posture state of a patient.

In another example, the disclosure relates to a system comprising means for receiving posture sensor data from a posture sensor; means for comparing the posture sensor data from the posture sensor to reference posture sensor data; and means for detecting at least one of sensor signal drift or sensor signal shift for the posture sensor based at least in part on the comparison, wherein the posture sensor data is indicative of a posture state of a patient.

The details of one or more examples of the invention are set forth in the accompanying drawings and the description below. Other features, objects, and advantages of the invention will be apparent from the description and drawings, and from the claims.

DETAILED DESCRIPTION

Figure 1:
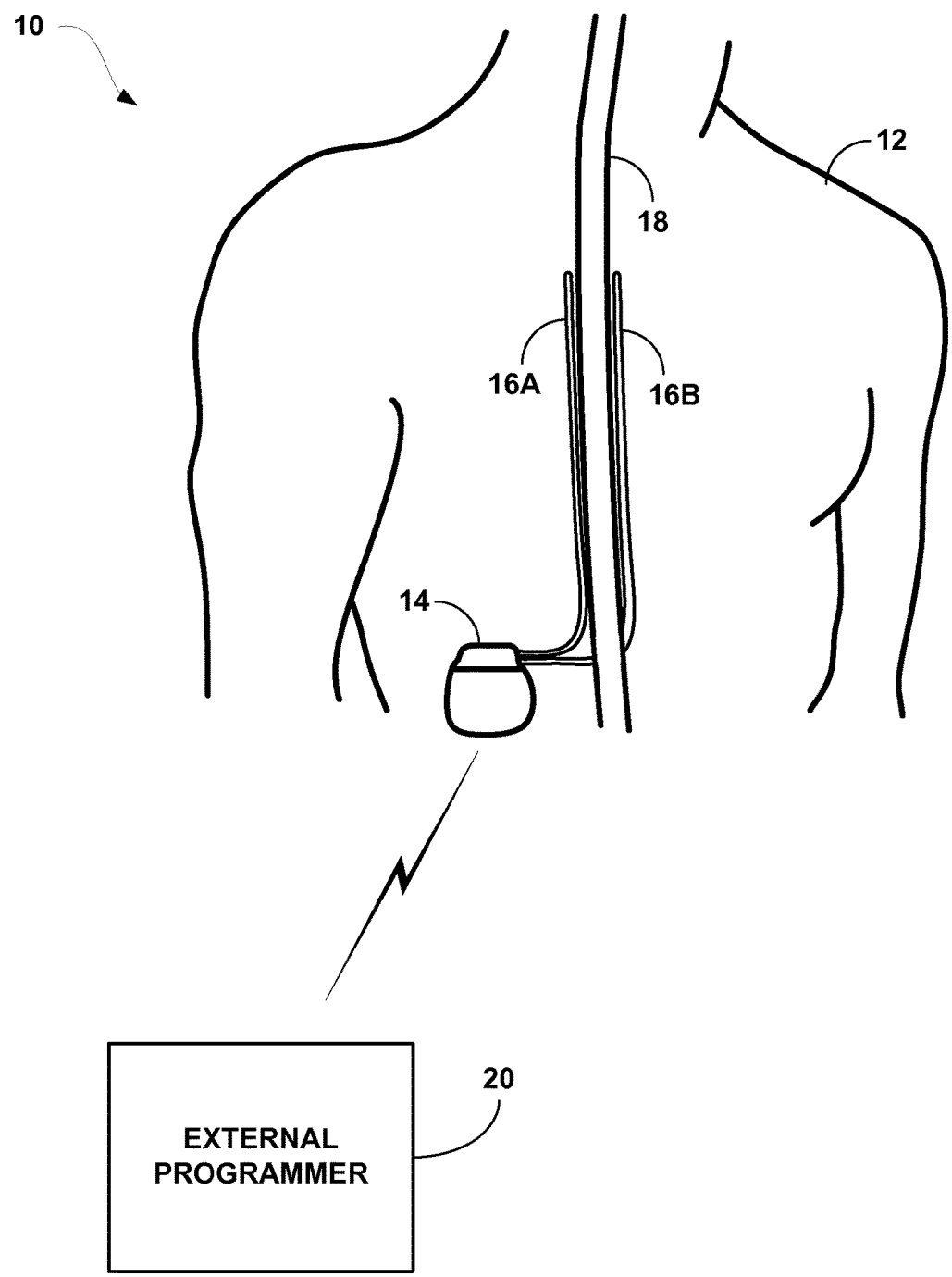
FIG. 1 is a conceptual diagram illustrating an example implantable stimulation system including two implantable stimulation leads.

In general, the disclosure relates to techniques for detecting signal shift and/or signal drift in the output of one or more postures sensors of a medical device. In some examples, the medical device may be an IMD that delivers electrical stimulation therapy to the patient. The IMD may detect the posture state of the patient via a posture state module and deliver medical therapy to the patient according to the detected posture state. For example, the IMD may automatically adjust one or more therapy parameter values or other characteristics of the therapy based on the detected posture state. To detect the posture state of a patient, a posture state module of an IMD or other medical device may include one or more posture sensors, such as, e.g., one or more accelerometers. The sensor output signal(s) generated by the one or more posture sensors of the posture state module may be indicative of patient posture state. For example, the posture state of a patient may be detected by comparing the sensor output signal(s) to posture state reference data that defines specific patient posture states.

In some examples, an offset signal shift and/or offset signal drift may be present in an output signal generated by the one or more posture sensors. An IMD or other medical device may detect the presence of the sensor signal offset shift and/or offset drift by comparing sensor data generated by a posture sensor to reference posture sensor data. Such a comparison may be performed for posture sensor data generated by the posture sensor when the patient occupies each of one or more posture states. In some examples, the reference posture sensor data is associated with one or more particular patient posture states. The reference posture sensor data may define sensor signal data, for example, for one or more particular posture state of the patient in which signal offset shift and/or drift is not substantially present or is present only in an insignificant and/or acceptable amount.

In some examples, upon detection of the offset shift and/or offset drift in the output of a posture sensor, the IMD or other medical device may determine and apply an offset correction to a posture state detection algorithm utilized to detect the posture state of the patient based on the output of the posture sensor. The applied offset correction may account for any inaccuracies in the detection of patient posture state that may result from offset signal shift and/or offset drift detected in the output of the posture sensor. Additionally or alternatively, an IMD or other medical device may suspend delivery of therapy to a patient on a posture state responsive basis or otherwise prevent delivery of posture responsive therapy to the patient, e.g., by preventing activation of posture responsive therapy delivery mode, until the detected offset shift and/or drift in the output of the posture sensor is addressed.

A medical device, such as an IMD, may deliver one or more types of therapy to patient, including electrical stimulation therapy and/or non-electrical stimulation therapy, such as therapeutic fluid delivery therapy. For purposes of illustration, the examples in this disclosure will be described with respect to the delivery of electrical stimulation therapy. However, it is understood that, in some examples, the same or similar principles may be applicable to the delivery of non-electrical stimulation therapy.

A medical device, such as an IMD, may deliver electrical stimulation therapy to a patient for a variety of reasons. For example, an IMD may deliver electrical stimulation therapy to treat patients that suffer from chronic back pain, leg pain, or other pain that cannot be effectively or efficiently treated through other methods. Generally, values for one or more stimulation parameters associated with the electrical stimulation therapy can be defined to treat one or more of the conditions experienced by a patient. However, as a patient changes posture states, which may include changes in posture and/or activity level, the stimulation therapy delivered by the IMD to the patient may have to be adjusted to maintain therapeutic efficiency. Efficacy refers, in general, to a combination of complete or partial alleviation of symptoms alone, or in combination with a degree of undesirable side effects.

In some cases, changes in posture state may cause changes in efficacy due to changes in distances between electrodes or other therapy delivery elements, e.g., due to temporary migration of leads or catheters caused by forces or stresses associated with different postures, or from changes in compression of patient tissue against leads or catheters in different posture states. Also, posture state changes may present changes in symptoms or symptom levels, e.g., pain level. For example, for some patients with a chronic lower back condition, sitting may be more painful than lying down. To maintain therapeutic efficacy, it can be desirable to adjust therapy parameters based on different postures and/or activities engaged by the patient to maintain effective therapy. As such, changes in therapeutic efficacy due to changes in posture state may require the patient to continually manage therapy by manually adjusting certain therapy parameters, such as amplitude, pulse rate, or pulse width in the case of stimulation therapy, or selecting different therapy programs to achieve more efficacious therapy throughout many different posture states.

In examples of therapy systems described herein, an IMD (or other medical device) employs one or more posture sensors that generate a signal(s) indicative of the patient posture state. In such case, the IMD may automatically modify the stimulation therapy being delivered to the patient based on the detected posture state change so as to maintain effective therapeutic results. The IMD may adjust therapy parameters in response to different posture states determined with the one or more posture sensors. An IMD may adjust therapy by modifying values for one or more therapy parameters, e.g., by specifying adjustments to a specific therapy parameter, or by selecting different therapy programs or groups of programs that define different sets of therapy parameter values.

Therapy adjustments in response to different posture states may be fully automatic, semi-automatic in the sense that a user may provide approval of proposed changes, user-directed in the sense that the patient may manually adjust therapy based on the posture state indication, or any combination of automation and user interaction. As one example, an IMD may adjust the values of one or more stimulation parameters of the stimulation therapy being delivered to a patient, e.g., stimulation amplitude value, to values that have been correlated to the posture state detected by the IMD for the patient. When a patient transitions from an upright to a lying posture, for example, the IMD may adjust the stimulation amplitude value from a value appropriate for the upright posture to a different value appropriate for the lying posture.

A posture state may refer to a patient posture or a combination of posture and activity. For example, some posture states, such as upright, may be sub-categorized as upright and active or upright and inactive. Other posture states, such as lying down posture states, may or may not have an activity component, but regardless may have sub-categories such as lying face up or face down, or lying on the right side or on the left side. Various posture states may be defined, at least in part, by different sets of posture state reference data. In some examples, posture sensor data received from a posture sensor when a patient occupies a particular posture state may be used to define, at least in part, posture state reference data corresponding to the respective posture state. The posture state reference data for a posture state may define, for example, a reference coordinate vector and a region around the reference coordinate vector. For example, the region around the reference coordinate vector may include a range of coordinates within a predetermined distance from the reference coordinate vector. In operation, a posture sensor module associated with the medical device compares posture sensor data to the posture state reference data to detect the posture occupied by the patient.

As one example, an IMD may utilize a posture state module, which may include a posture sensor, to detect the posture state of a patient. To detect the posture state of a patient, the posture state module may receive posture sensor data generated by one or more posture sensors and compare the posture sensor data to posture state reference data. In the case of a posture state module including a three-axis accelerometer sensor, the posture sensor data generated by the one or more posture sensors may comprise a coordinate vector in a 3-dimensional space, e.g., as determined from the sensor signals for each of the x, y, and z-axis. The posture state reference data may define a reference coordinate vector and a range of coordinates within a predetermined distance from the reference coordinate vector for the 3-dimensional space. In such a case, the posture state reference data may, in effect, define a posture volume or zone, such as, e.g., a posture cone. The posture cone, and the range of vector coordinates within the cone, may be defined in a variety of ways. For example, the posture cone may be defined by a distance or angle relative to the reference coordinate vector. As an alternative, a range of cosine values may define vectors within the cone in the sense that a cosine value computed for each of the vectors in the cone and the reference coordinate vector falls within the range of cosine values.

If the posture sensor data indicates a coordinate vector that falls within the range of coordinates defined by the posture state reference data for the 3-dimensional space, the IMD determines that the patient occupies the posture state associated with the posture state reference data. If the coordinate vector indicated by posture sensor data falls within the range of posture coordinates specified by the posture state reference data corresponding to an upright posture state, for example, then the IMD may detect that the patient is in the upright posture state. Different posture states may be associated with different sets of posture state reference data. The posture sensor data may be compared to multiple sets of posture state reference data until a matching posture state is detected. In some examples, however, posture sensor data may fall within undefined areas that do not match any posture state reference data.

To initially define a set of posture state reference data for a particular posture state, a patient may occupy the posture state. While the patient occupies the posture state, the posture state (e.g., lying back, lying front, lying right, lying left, or upright) may be communicated to the IMD, e.g., from an external programmer via wireless telemetry. Then, the IMD may define posture state reference data for the posture state based on the posture sensor data obtained from the posture sensor(s) while the patient is in the indicated posture state. In this manner, the IMD may define a set of posture state reference data based on the posture sensor data that is actually produced while the patient is in the respective posture state.

Once posture state reference data is defined for a posture state, the IMD may detect when a patient is occupying that posture state based on a comparison of the posture sensor data to the posture state reference data for the posture state. If there is a match between the posture sensor data generated by the posture sensor and the posture state reference data, then the IMD detects the patient is in the pertinent posture state. The orientation process may be repeated for each of the posture states of the patient that are desired to be detected, or for a subset of the posture states sufficient to determine posture state reference data for all posture states.

In some instances, offset shift and/or offset drift may be present in the signal output generated by a posture sensor. Signal offset shift may include one or more distinct parametric shifts in the signal output that may occur at one or more discrete points in time. Hence, signal offset shift may result from some acute change in the sensor or its disposition on or within a patient. Signal offset drift may include one or more parametric shifts that may more gradually accumulate in the output of a sensor signal over an extended period of time. In some cases, shift or drift may be caused by gradual changes in electronic components within an accelerometer or associated sensor circuitry or by an acute force that is significant enough to displace sensing elements. In each case, the presence of offset shift and/or drift may cause a parametric change in the signal output generated by a posture sensor. Such parametric changes may include shifts in signal amplitude, e.g., voltage or current, such as a shift in the amplitude of a signal corresponding to one or more axes of an accelerometer. For example, in the case of an accelerometer that generates a voltage output signal to indicate acceleration along a particular axis, the presence of an offset shift or drift may cause a parametric shift in the voltage of the signal generated by the accelerometer for the axis. For ease of illustration, offset signal drift and/or offset signal shift may be referred to herein in some instances as offset shift/drift.

When offset shift/drift is present in the output signal of one or more posture sensors, the ability of an IMD to detect the actual posture state occupied by a patient may be impacted. An example illustrating the influence that an offset shift/drift in the signal output of one axis of a three-axis accelerometer is described below with regard to FIGS. 9A-D. In some cases, the presence of offset shift/drift may cause the IMD to inaccurately detect the posture state of the patient, in which case the IMD may modify the therapy inappropriately. For example, the IMD could unnecessarily adjust one or more therapy parameters and/or fail to adjust one or more therapy parameters due to difference between the actual posture state of the patient and the posture state detected by the IMD in the presence of offset shift/drift. Accordingly, therapeutic efficacy may be impacted if offset shift/drift is not taken into account by IMD when detecting the posture state of the patient.

In accordance with this present disclosure, in some examples, an IMD or other medical device (e.g., external programmer) may be configured to detect the presence of offset shift/drift in the sensor output generated by one or more posture sensors of a posture state module. The presence of offset shift/drift may be detected by comparing posture sensor data generated by one of more posture sensors to reference posture sensor data. In some examples, the comparison of the posture sensor data from the posture sensor to the reference posture sensor data may allow differences between the posture sensor data and baseline posture sensor to be determined. Differences between the reference posture sensor data and the posture sensor data generated by the posture sensor may be indicative of the presence of offset shift/drift in the signal generated by a posture sensor. In some examples, to detect the presence of offset shift/drift in the output of a posture sensor, the IMD or other medical device may compare posture sensor data generated by a posture sensor for each of a plurality of posture states assumed by the patient to reference posture sensor data. Reference posture sensor data may be associated with each particular posture states of a patient. In such cases, for each posture state assumed by the patient, posture sensor data generated by a posture sensor when the patient occupies the posture state may be compared to the reference posture sensor data associated with that posture state. Reference posture sensor data may be substantially the same for a plurality of different posture states (e.g., substantially the same reference posture state data may be associated with substantially all patient posture states) or reference posture sensor data may be different for each of a plurality different posture states. For example, certain posture states may have reference posture sensor data that is unique to a respective posture state or reference posture sensor data may be generally applicable to all posture states that may be occupied by a patient.

The posture sensor data used to detect offset shift/drift may include values for one or more measurable parameters of the output signal generated by a posture sensor, especially those parameters used to determine the posture state of a patient. In some examples, a posture sensor used by an IMD to detect patient posture set may include an accelerometer sensor. For ease of description, examples of the disclosure are described primarily with regard to a 3-axis accelerometer as the posture sensor that generates an output signal for each axis, i.e., an output signal for each of the x, y, and z axis. However, examples of the disclosure are not limited as such. In some examples, an IMD may detect patient posture state via multiple single-axis accelerometers, dual-axis accelerometers, 3-axis accelerometers, or some combination thereof, or may include a sensor other than an accelerometer. In the case of a 3-axis accelerometer, posture sensor data may include a signal value sampled from the output signal for each axis generated by the accelerometer. In some examples, the signal value for one or more of the axes may be an average value determined based on a plurality of sampled signal values. Additionally or alternatively, posture sensor data may include a magnitude and/or angle of a posture vector derived from the values of each axis of the accelerometer sensor within a 3-dimensional vector space.

An IMD may determine posture sensor data for one or more posture states of the patient by measuring the output signal values for each axis of an accelerometer sensor when the patient actually occupies the respective posture state. For example, while a patient occupies a standing posture state, posture sensor data (e.g., x, y, and z axis values and/or vector magnitude) may be defined for the standing posture state at that point in time based on the measured values for each output signal generated by the accelerometer sensor for each of the x, y, and z axis. As described above, such posture sensor data may also be used, for example, by an IMD to determine the posture state of a patient as well as to detect the presence of offset shift/drift in a posture sensor signal.

In some examples, posture sensor data for each of a plurality of different posture states may be compared to reference posture sensor data to detect the presence of offset shift/drift in the output of posture sensor. As will be described further below, in some examples, such as those examples in which the posture sensor includes a multi-axis accelerometer sensor, the plurality of posture states used for the generation of posture sensor data may include postures states of the patient that are distributed throughout a multi-dimensional posture state zone or space within which the multi-axis posture sensor output resides. In some examples, the plurality of posture states may include two or more posture states that are approximately orthogonal to one another, e.g., within approximately 30 degrees of orthogonal to each other, such as, within approximately 20 degrees of orthogonal to each other or approximately 10 degrees of orthogonal to each other. In some examples, the two or more postures state may be substantially orthogonal to each other, e.g., within approximately 5 degrees of orthogonal to each other.

As an illustration, for a situation in which the posture sensor generates outputs along x, y, and z-axis within a three-dimensional posture space, posture sensor data may be received for each of a plurality of posture states distrusted throughout all or a portion of the three-dimensional posture state space. In one example, the plurality of posture states may include respective posture states that are approximately orthogonal to each other in the three-dimensional posture space. For example, first, second, and third posture sensor data may be defined by the output of the posture sensor while the patient actually occupies an upright, lying back, and lying left posture states, respectively. Such patient posture states may be approximately orthogonal to each other in the three-dimensional posture state space of the posture sensor output. The first, second, and third posture sensor data may then be compared to reference posture sensor data. As described above, the posture sensor data may be the same or different for each posture state. Based on the comparison, the presence of offset shift/drift along one, two, or all three axes in the output of the posture sensor may be detected. As will be described below, in some examples, the first, second, and third posture sensor data may then be used to determine offset correction values for one, two, or all three axis of the sensor output to correct for the detected offset shift/drift in the output of the posture sensor.

The reference posture sensor data used by an IMD to detect signal offset shift/drift by way of comparison to the posture sensor data received from a posture sensor may be representative of the posture sensor data in which offset shift and/or drift is not present in the output signal of the posture sensor or is present only in an insignificant and/or acceptable amount, e.g., as defined by a clinician or device manufacturer. In this manner, any differences between the reference posture sensor data and the posture sensor data actually received when the patient occupies similar posture states may be indicative of the presence of signal offset shift/drift. If in the case where the position of the patient in a posture state can be accurately replicated during the time that the reference posture sensor data is acquired and the during the time that the current posture sensor data is acquired, then the reference posture sensor data and the current posture sensor data may include x, y, and z-axis output for each of the plurality of posture states. In other cases, e.g., where the postures states cannot be accurately replicated (e.g. due to in ability to position patient accurately) then the reference posture sensor data and the current posture sensor data may include characteristic information, such as the magnitude of a posture vector derived from each individual value of the x, y, and z-axis within a three-dimensional posture space.

In some examples, the reference posture sensor data may include baseline posture sensor data defined by actual sensor data generated by the posture sensor at some previous time. For example, for a particular posture state, reference posture sensor data may include baseline posture sensor data defining the actual output of the posture sensor when the patient occupied approximately the same posture state at some earlier time, e.g., during an initial programming session after an IMD is implanted. The previous time at which the baseline sensor signal data is defined may generally correspond to a period of time when offset shift/drift was not substantially present in the sensor output signal or was present only in a relatively insignificant and/or acceptable amount. Differences in current posture sensor data for one or more posture states relative to the baseline posture sensor data may be attributed to the presence of offset shift/drift in the signal output of the posture sensor.

Alternatively or additionally, the reference posture sensor data may be predetermined by a user, such as, e.g., a clinician. For example, reference posture sensor data may be defined based on or more values estimated or otherwise known to be representative of the actual posture sensor data for a posture state when substantially no offset shift/drift is present. In some examples, such reference posture sensor data may be defined by manufacturer based on specification values for an accelerometer device or previous patient(s) in which substantially the same or similar posture sensor has been used. In some examples, the reference posture sensor data may be determined from sampling of the sensor signal prior to implantation of the IMD, e.g., during a trial stimulation period or during that manufacturing process of the IMD. As the output signals for each axis of a multiple axis accelerometer can depend on the physical orientation of the accelerometer in a patient, the average magnitude of the vector derived from the signal values for each axis observed in other patients and/or otherwise defined for the particular accelerometer may be used as reference posture sensor data rather than output signal values for each individual axis. In such examples, one or more posture vector magnitudes may be used to define reference posture sensor data for more than one posture states of a patient.

Analysis of posture sensor data for offset shift/drift may be performed by an IMD or other medical device on a substantially continuous or periodic basis. In some examples, a medical device may automatically or semi-automatically (e.g., based on user confirmation of a request generated by the medical device) analyze posture sensor data to detect the presence of offset shift/drift in a posture sensor signal output. Alternatively or additionally, a medical device system may analyze posture sensor data for offset shift/drift upon receipt of a user request, e.g., a user request communicated to an IMD via an external programming device. The posture sensor data may be analyzed for offset shift/drift initially upon implantation of an IMD in a patient, e.g., during an initial programming session. In such cases, reference sensor data may not be defined based on actual posture sensor data measured for the posture sensor when implanted in the patient. In some examples, a posture sensor may be evaluated prior to implantation, e.g., during a trial stimulation period when the posture sensor is used by an external trial stimulator device to detect patient posture state, to prevent implantation of a posture sensor device exhibiting offset shift/drift in an output signal generated by the posture sensor for cases in which the posture sensor to be implanted is the same sensor that is used during the trial stimulation period.

If offset shift/drift is detected in an output signal from one or more posture sensors, the IMD or other medical device may determine and apply an offset correction to the sensor signal data generated by the posture sensor to address any inaccuracies in the detection of patient posture state that may result from the detected offset signal drift and/or shift. For example, in the case of an offset shift/drift being present in the output signal of only a single axis of a 3-axis accelerometer, an offset correction value may be determined for one or more of the three axes of posture sensor to account for the detected offset shift/drift. Such offset correction values may be applied to a posture detection algorithm used to analyze posture sensor data to detect the posture state of the patient to allow the IMD to accurately detect the posture state of the patient even though the offset shift/drift is present in the output of the posture sensor used to generate the posture sensor data.

FIG. 1 is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers SCS, e.g., for relief of chronic pain or other symptoms. Again, although FIG. 1 shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to treat tremor, Parkinson's disease, epilepsy, urinary or fecal incontinence, pelvic pain, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy. In these cases, the leads may be implanted in different locations other than the spinal cord.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 12 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that is used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms, e.g., pain or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include one or more posture sensors such as an accelerometer sensor that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

The postures sensor used by IMD 14 to determine the posture state of patient 12 may be susceptible to offset signal drift and/or offset signal shift in the sensor signal output. As will be described further below, IMD 14 may be configured to detect the presence of signal offset shift/drift in the output signal(s) generated by the one or more posture sensors used to detect patient posture state. IMD 14 may be programmed to automatically or semi-automatically analyze the posture sensor for offset shift/drift on a continuous or periodic basis. In some examples, patient 12 or another user may direct IMD 14 to analyze the posture sensor used by IMD 14 to detect the patient posture state via external programmer 20, e.g., as a precautionary measure or based on the perception of reduced therapeutic efficacy by patient 12.

To detect offset shift/drift in the posture sensor, IMD 14 may receive posture sensor data generated by the posture sensor when patient 12 occupies a posture state and compare the received posture sensor data to reference posture sensor data. Such an analysis may be repeated by IMD 14 for a plurality of different patient posture states to detect the presence of signal offset shift/drift in the output of the posture sensor of IMD 14. For example, IMD 14 may receive posture sensor data for each of a plurality posture states occupied by patient 12, and then, for each posture state, compare the posture sensor data for the posture states to reference posture sensor data. In some examples, the plurality of posture states may include multiple posture states that are approximately orthogonal to each other within a posture space in which the posture sensor data is used to detect patient posture state. Approximately orthogonal posture states may be posture states that are within approximately 30 degrees, such as, e.g., within approximately 20 degrees or approximately 10 degrees, of orthogonal to each other within the posture state space of the posture sensor output. In this manner, any differences between the reference posture sensor data and the current posture sensor data actually received when the patient occupies similar posture states may be indicative of the presence of signal offset shift/drift. If in the case where the position of the patient in a posture state can be accurately replicated during the time that the reference posture sensor data is acquired and the during the time that the current posture sensor data is acquired, then the reference posture sensor data and the current posture sensor data may include x, y, and z-axis output for each of the plurality of posture states. In other cases, e.g., where the postures states cannot be accurately replicated (e.g. due to in ability to position patient accurately) then the reference posture sensor data and the current posture sensor data may include characteristic information, such as, e.g., the magnitude of a posture vector derived from each individual value of the x, y, and z-axis within a three-dimensional posture space. In some examples, substantially the same posture vector magnitude may be applicable as reference posture sensor data for each posture state of the patient. In some examples, if an offset shift/drift is detected by IMD 14, IMD 14 may determine an offset correction that properly accounts for the detected offset shift/drift, and apply the offset correction to a posture state detection algorithm used by IMD 14 to detect the posture state of patient 12 based on the output of the posture sensor.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 2:
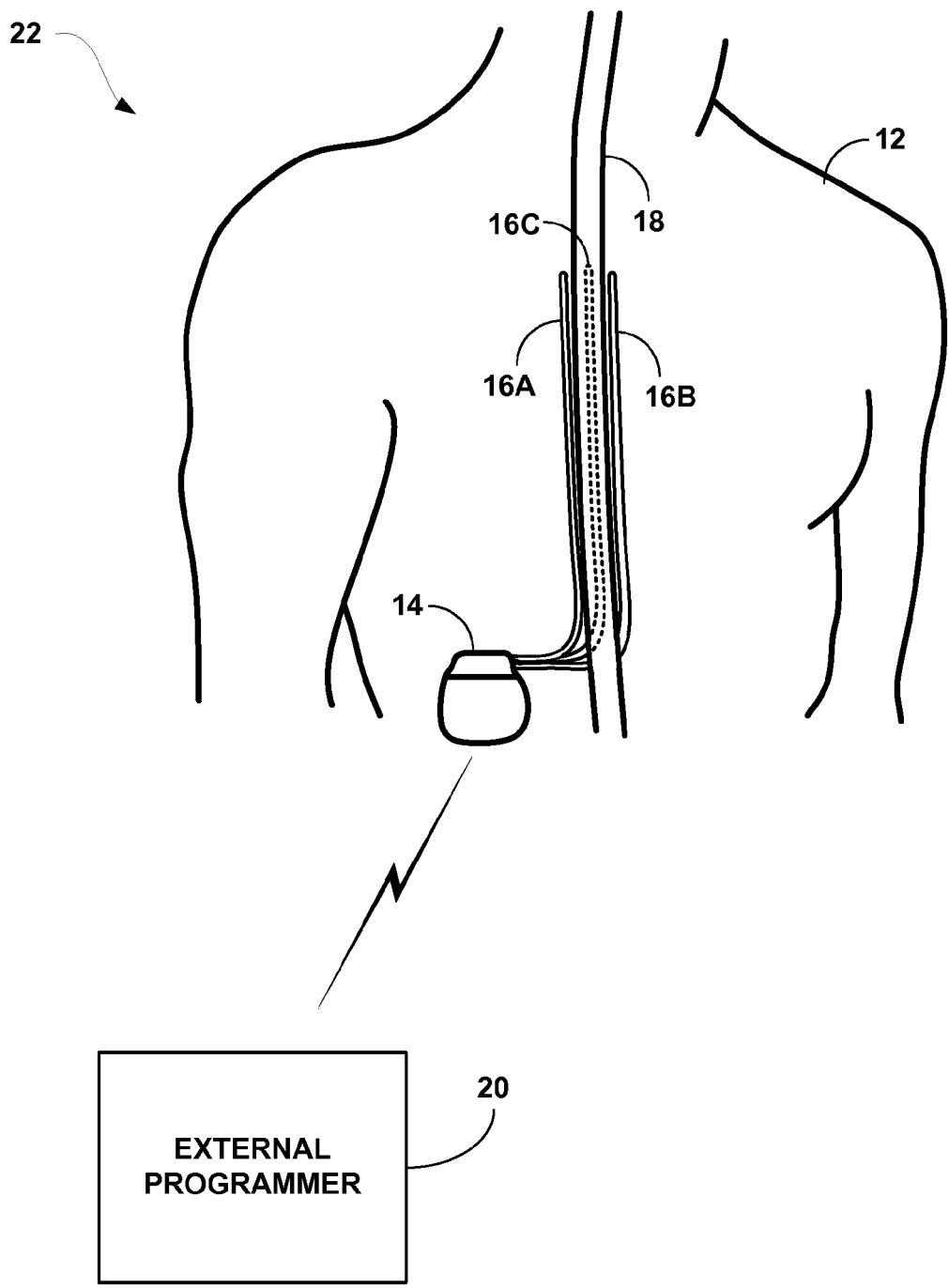
FIG. 2 is a conceptual diagram illustrating an example implantable stimulation system including three implantable stimulation leads.

FIG. 2 is a conceptual diagram illustrating an implantable stimulation system 22 including three implantable stimulation leads 16A, 16B, 16C (collectively leads 16). System 22 generally conforms to system 10 of FIG. 1, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 3:
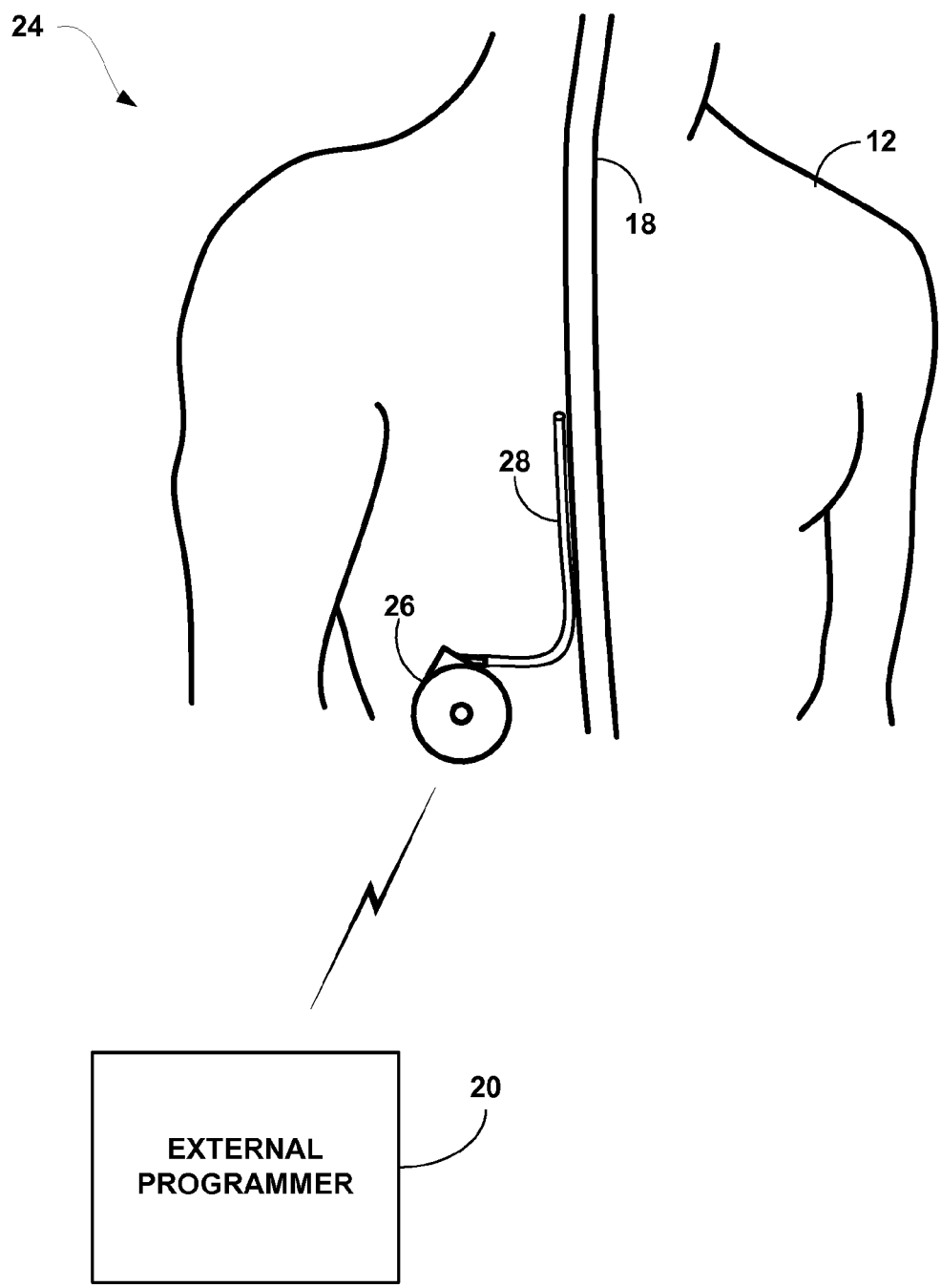
FIG. 3 is a conceptual diagram illustrating an example implantable drug delivery system including a delivery catheter.

FIG. 3 is a conceptual diagram illustrating an implantable drug delivery system 24 including one delivery catheter 28 coupled to IMD 26. As shown in the example of FIG. 3, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 3, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1) and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 includes a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Also similar to IMD 14, a processor of IMD 26 (or processor of another device) may analyze posture sensor data generated by a posture sensor to detect whether offset drift/shift is present in the posture sensor output using one or more of the techniques described in this disclosure. In some examples, if offset shift/drift is determined to be present in the posture sensor output signal, IMD 26 may determine an offset correction that properly accounts for the detected offset shift/drift and applies the offset correction to a posture state detection algorithm used by IMD 26 to detect the posture state of patient 12 based on the output of the posture sensor.

Figure 4:
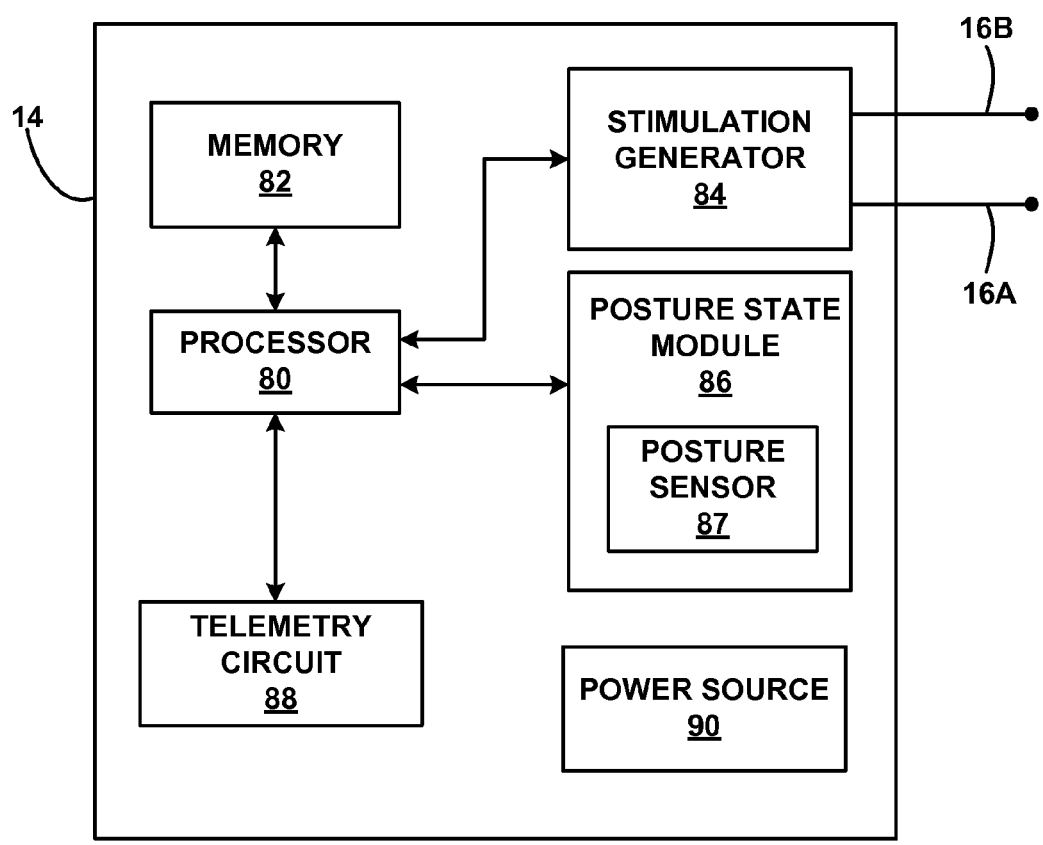
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12.

Memory 82 may store reference posture sensor data for one or more posture states of patient 12 as well as, for one or more posture states of patient 12, actual posture sensor data generated by the posture sensor of posture state module when patient 12 occupies a respective posture state. As described herein, such stored posture sensor information may be used to detect offset shift/drift in a signal generated by a posture sensor. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and approximately 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications. Parameter values and ranges of values other than the example values described above are contemplated.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes posture sensor 87 that generates one or more sensor signals that may be used to detect the posture state of patient 12. In some examples, postures sensor 87 may include one or more accelerometers, such as a three-axis accelerometer, capable of detecting static orientation or vectors in three-dimensions (e.g., x, y, z coordinate vectors). Example accelerometers may include a micro-electro-mechanical systems (MEMS)-based accelerometer. In other examples, posture state module 86 may alternatively or additionally include posture sensor 87 in the form of one or more gyroscopes, piezoelectric crystals, pressure transducers or other sensors to sense the posture state of patient 12. Posture sensor data generated by posture state module 86 via posture sensor 87 and processor 80 may correspond to an activity and/or posture undertaken by patient 12 or a gross level of physical activity, e.g., activity counts based on footfalls or the like.

Posture sensor data from posture state module 86 may be stored in memory 82 for later review by a clinician, used to adjust therapy, present a posture state indication to patient 12 (e.g., via patient programmer 30) or some combination thereof. As an example, processor 80 may record one or more posture sensor parameter values, or output, of the 3-axis accelerometer as posture sensor data and use the posture sensor data to form posture state reference data for a certain predefined posture indicated by the posture sensor data. Using the posture sensor data from posture state module 86, IMD 14 may be able to track how often patient 12 remains within a certain posture.

Memory 82 may include definitions for each posture state of patient 12 based on posture state reference data. In one example, the definitions of each posture state may be illustrated as a cone in three-dimensional space. Whenever the posture sensor data, e.g., a coordinate vector, from the three-axis accelerometer of posture state module 86 resides within a predefined cone defined by the posture state reference data, processor 80 indicates that patient 12 is in the posture state of the cone. In other examples, posture sensor data from the 3-axis accelerometer may be compared to a look-up table or applied to an equation to determine the posture state in which patient 12 currently resides.

IMD 14 may also store which group or program was being used to deliver therapy when patient 12 was in the sensed posture. Further, processor 80 may also adjust therapy for a new posture when posture state module 86 indicates that patient 12 has in fact changed posture states. Therefore, IMD 14 may be configured to provide posture-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

Posture-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

Processor 80 may record one or more posture sensor parameter values, or output, of the 3-axis accelerometer as posture sensor data and use the posture sensor data to define reference posture sensor data in the form of baseline posture sensor data for the posture state that patient 12 occupied when the signal output was generated by posture sensor 87. Such baseline posture sensor data may be compared to sensor data sensed at a later time when patient 12 occupies approximately the same posture state to detect the presence of offset shift/drift in the output signal of posture sensor 87. In some examples, the baseline posture sensor data may be used to define reference posture sensor data for posture states other than that of the posture state occupied by patient 12 when the output of the posture sensor was recorded. For example, processor 80 may define a "typical" magnitude of a posture vector derived from the outputs of each of the x, y, and z axes of posture sensor 87 for when patient occupies multiple posture states, e.g., multiple posture states that are approximately orthogonal to one another, such as, e.g., upright, lying back, and lying left posture states. In some examples, the "typical" magnitude may be an average of the posture vector magnitudes derived from the output of a posture sensor for two or more posture state occupied by patient 12 or even from a single posture state of patient 12, e.g., when the posture vector magnitude is known to be substantially that same in each posture state. The "typical" reference vector magnitude can then be compared against any future posture vector magnitude acquired when patient 12 is in a different posture state than the one or more posture states that were used to define the reference posture sensor data. If the "typical" reference vector magnitude and the current vector magnitude is different, or greater than a difference threshold, then processor 80 may determine that an offset shift/drift is present. Using the "typical" reference vector magnitude and the current posture state data, processor 80 may determine one or more offset correction values that may be applied to account for the detected offset shift/drift in the signal generated by posture sensor 87. Processor 80 may store an offset correction value in memory 82 for application to posture sensor data when analyzed by processor 80 via a posture state detection algorithm to determine the posture state of patient 12 at a later time.

Although posture sensor 87 is described in some instances as including a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the posture state of patient 12 may be determined from multiple posture sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of posture sensor 87 in posture state module 86 to determine activity and/or posture data. For example, where posture sensor 87 comprises an accelerometer, processor 80 or a processor of posture state module 86 may process the raw signals generated by posture sensor 87 to determine activity counts. In some examples, processor 80 may process the signals provided by the posture sensor 87 to determine velocity of motion information along each axis.

In one example, each of the x, y, and z axis signals generated by posture sensor 87 has both a DC component and an AC component. The DC components describes the gravitational force exerted upon sensor 87 and can thereby be used to determine orientation of the sensor within the gravitational field of the earth. Assuming the orientation of the sensor is relatively fixed with respect to the patient, the DC components of the x, y and z axis signals may be utilized to determine the patient's orientation within the gravitational field, and hence to determine the posture of the patient, assuming proper orientation of the sensor to the patient's body.

The AC component of the x, y and z axis signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a coordinate vector and an associated tolerance, which may be a distance from the coordinate vector. Another example of an activity parameter value relates to acceleration. The value quantifying a level of change of motion over time in a particular direction may be associated with this parameter referenced in the activity parameter value.

IMD 14 wireless communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like. The information transmitted and received from external programmer 20 may include posture sensor data and/or other information used to detect offset shift/drift in the signal output of posture sensor 87 as well as information used to determine one or more offset correction values to account for a detected offset shift/drift.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
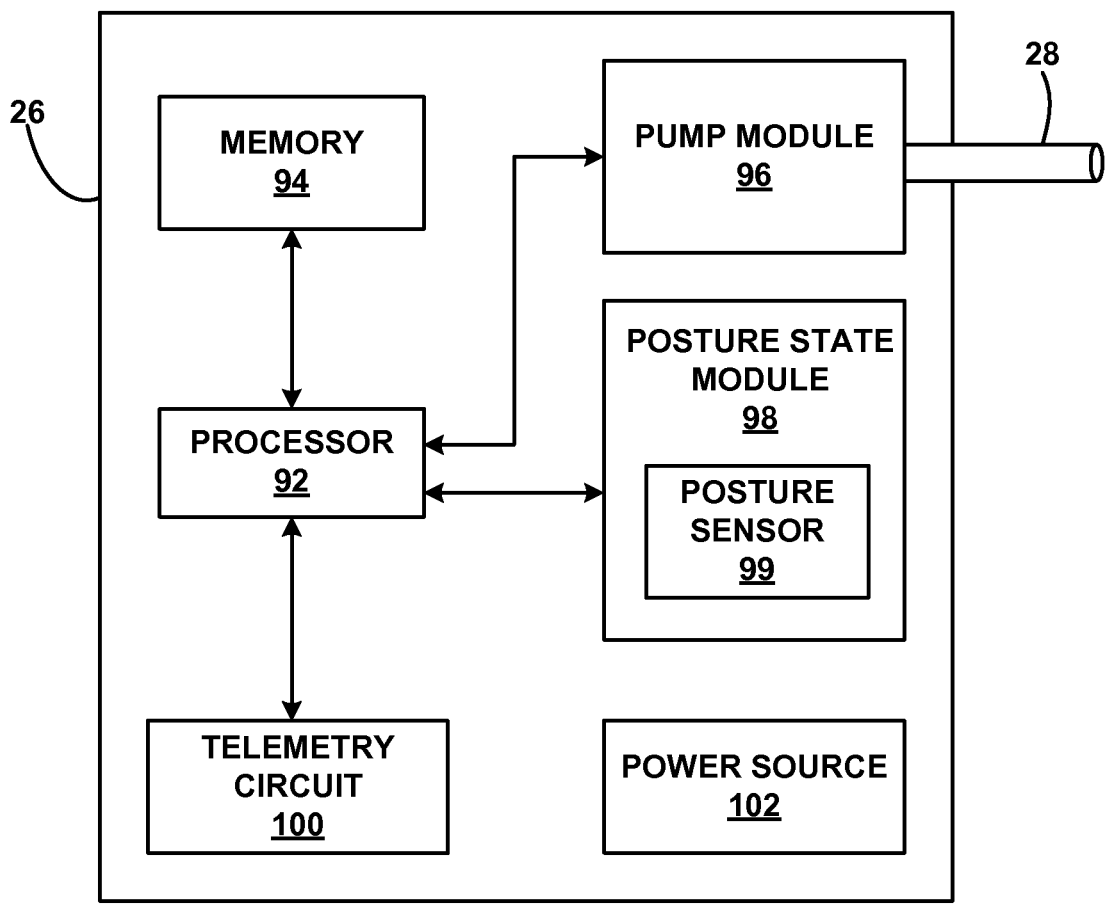
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Posture state module 98 include posture sensor 99. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture.

Figure 6:
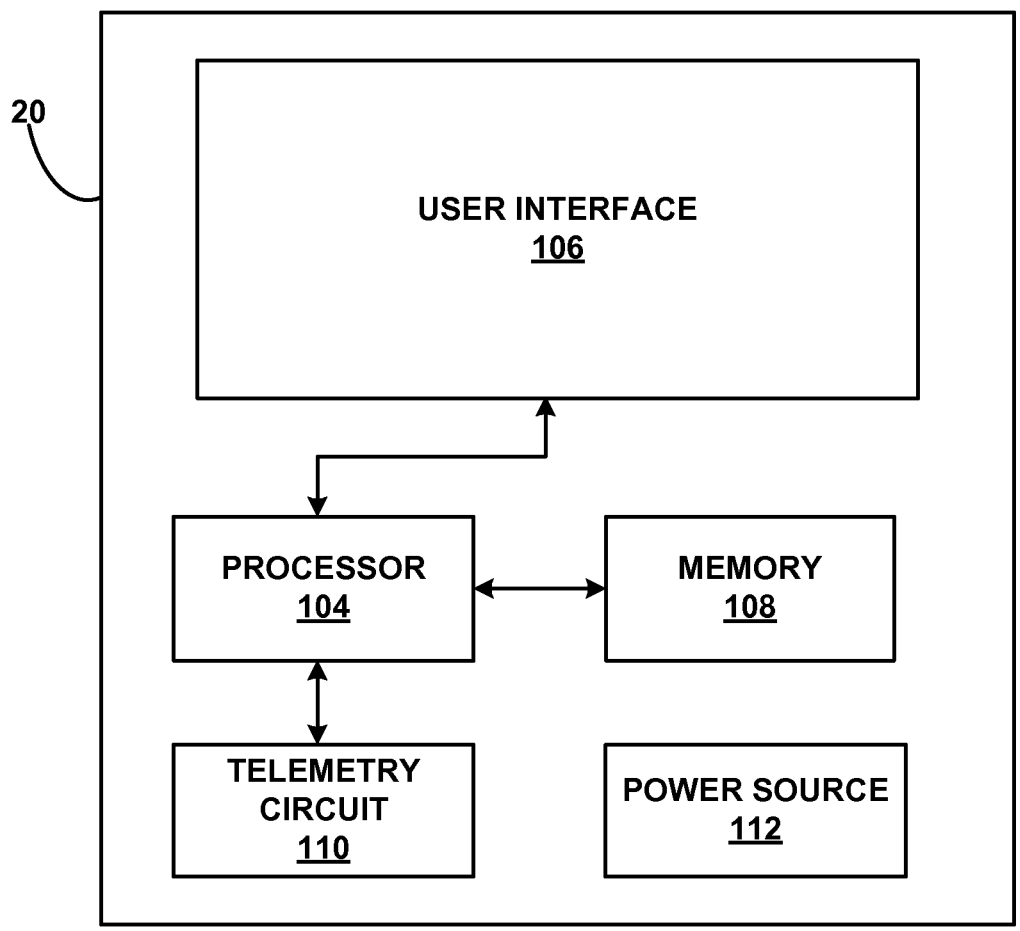
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112.

In some examples, external programmer 20 may be embodied as a patient programmer or a clinician programmer. External programmer 20 may provide a user interface 106 for a user, such as a patient 12, clinician, physician, technician, or nurse, to manage and program stimulation therapy. As a patient programmer, programmer 20 may accompany patient 12 throughout a daily routine. In some cases, programmer 20 may be used by a clinician when patient 12 visits the clinician in a hospital or clinic. In other examples, programmer 20 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Using programmer 20, a user may program stimulation therapy (e.g., selecting stimulation parameter values), modify programs or groups, retrieve stored therapy data, retrieve posture state information from an IMD or another device, define posture states and other activity information, or any other therapy related function. In addition, programmer 20 may be capable of communicating with a networked server in order to send or receive an email or other message, retrieve programming instructions, access a help guide, send an error message, or perform any other function that may be beneficial to prompt therapy.

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. In some examples, memory 108 may store information for one or more therapy programs used to define therapy delivered from IMD 14 to patient 12. Additionally or alternatively, therapy program information may be stored in memory 82 of IMD 14. Memory 108 also includes instructions for generating and delivering programming commands to IMD 14, such as a programming command that instructs IMD 14 to activate or deactivate a posture-responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12, or another user (e.g., a patient caretaker) interacts with user interface 106 in order to manually change the stimulation parameter values of a program, change programs within a group, turn posture-responsive stimulation ON or OFF, view therapy information, view posture state information, or otherwise communicate with IMDs 14 or 26.

User interface 106 may include a screen and one or more mechanisms, such as, buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
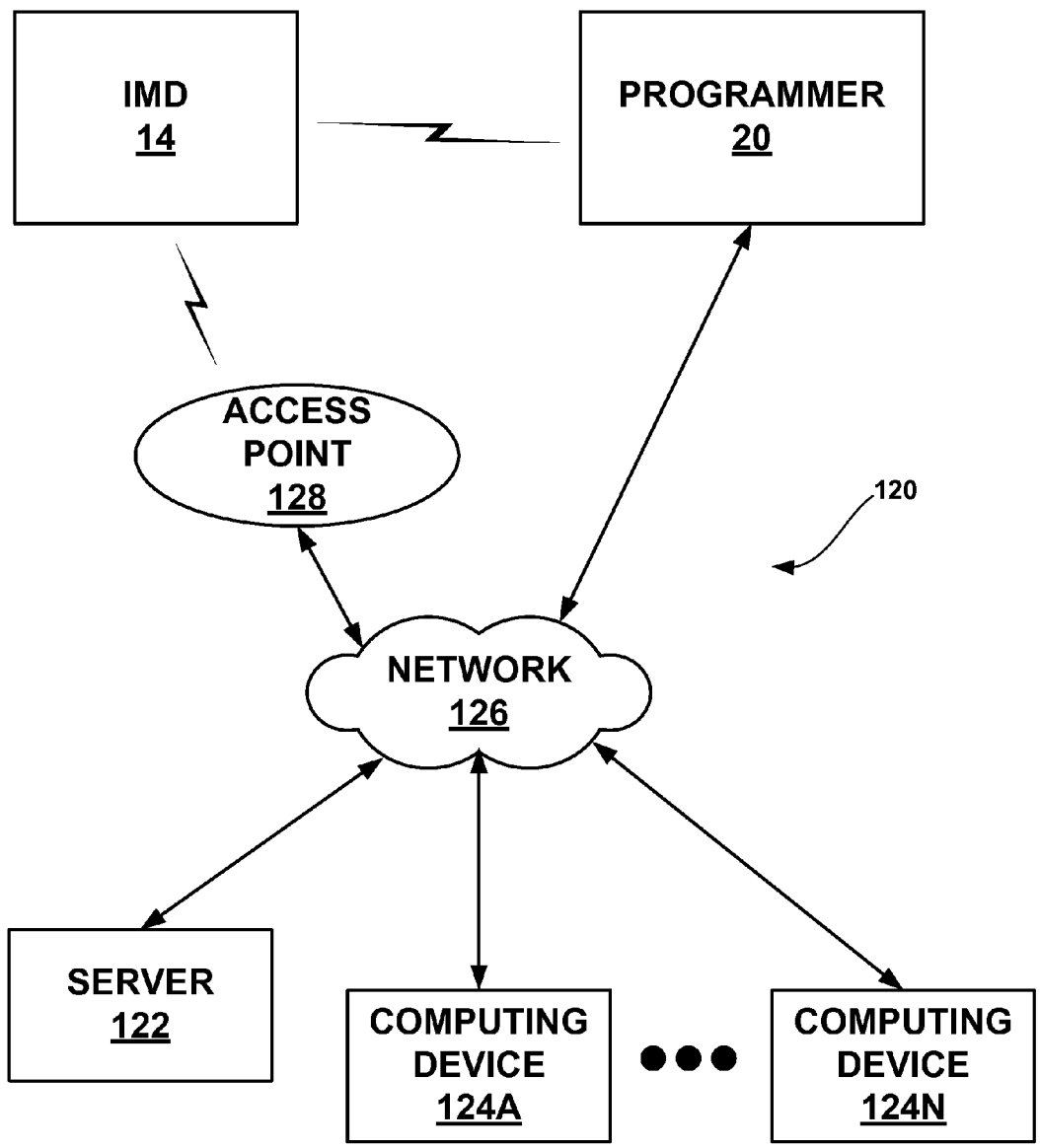
FIG. 7 is a functional block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician In some cases, IMD 14, external programmer 20 or server 122 may process posture sensor information, posture sensor data, and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In some examples, IMD 14 may collect and store posture sensor data used for the detection of offset drift/shift in posture sensor 87. In some cases, IMD 14 may directly analyze the collected data to detect offset shift/drift and/or determine offset correction value(s) to correct the detected offset drift/shift. In other cases, however, IMD 14 may send posture sensor data to external programmer 20 and/or server 122, either wirelessly or via access point 128 and network 126, for remote processing and analysis. This communication may occur in real time, and network 126 may allow a remote clinician to review the stored posture sensor data, e.g., via computing device 124A.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture sensor data and other posture state information, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture sensor data, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
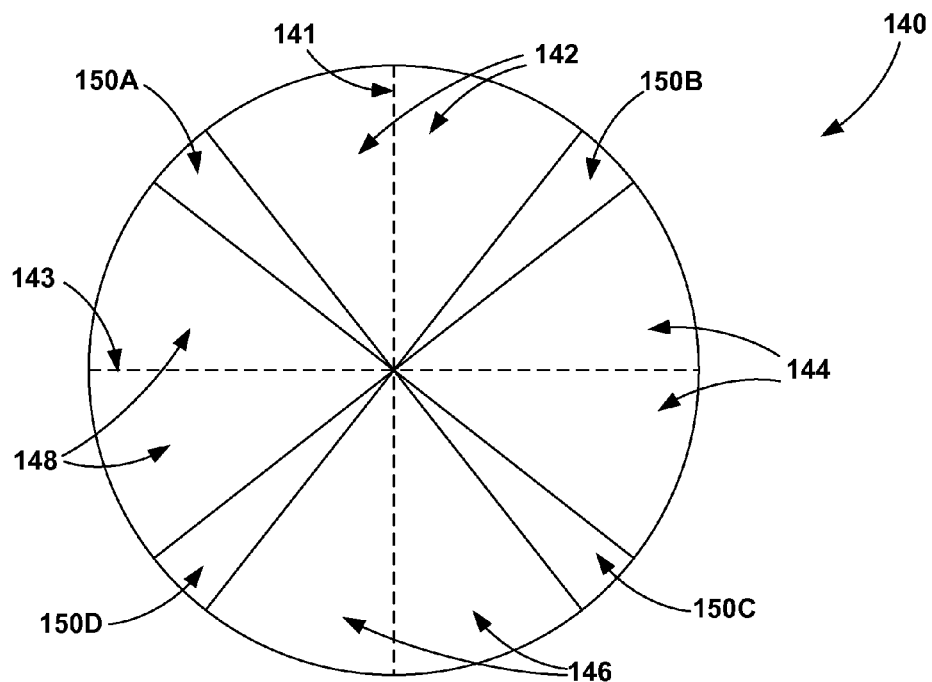
FIGS. 8A-8C are conceptual diagrams illustrating example posture state spaces within which postures state reference data may define the posture state of a patient.
Figure 8B:
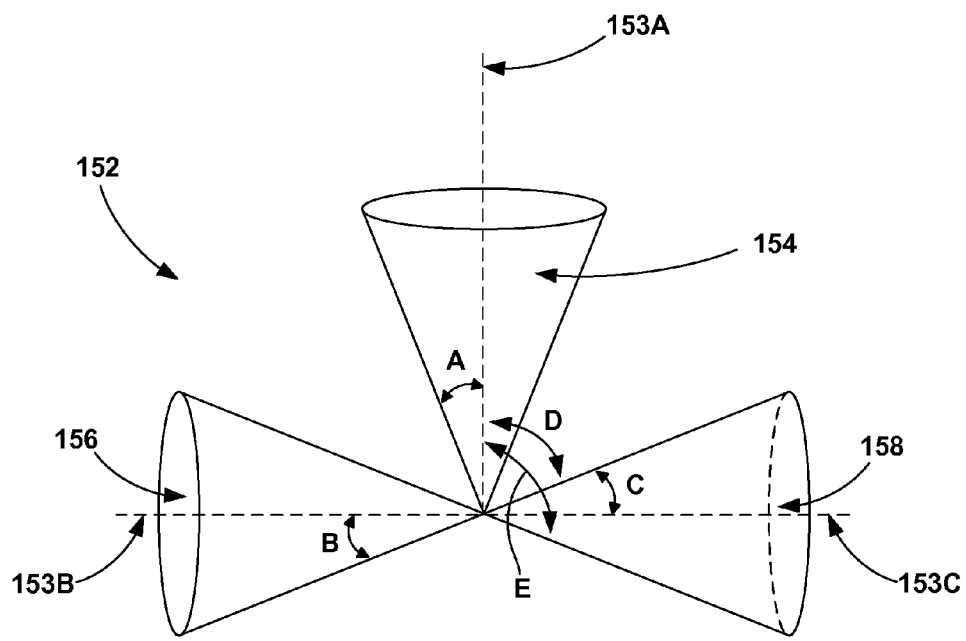
Figure 8C:
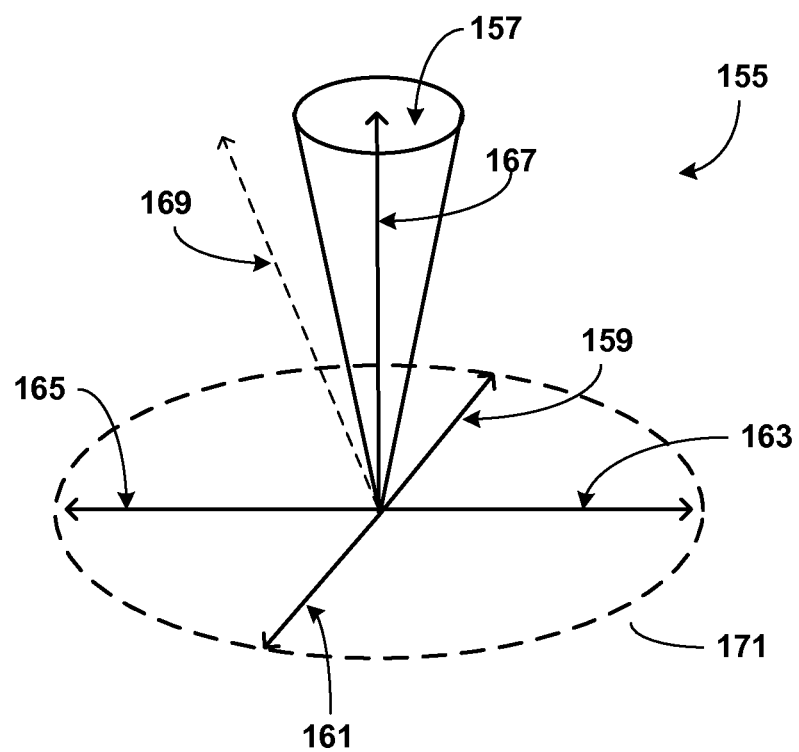

FIGS. 8A-8C are conceptual diagrams illustrating example posture state spaces 140, 152, 155 within which posture state reference data may define the posture state of patient 12. Posture state reference data may define certain regions associated with particular posture states of patient 12 within the respective posture state spaces 140, 152, 155. The output of posture sensor 87 may be analyzed by posture state module 86 with respect to posture state spaces 140, 152, 155 to determine the posture state of patient 12. For example, if the output of posture sensor 87 is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from posture sensor 87 of a posture state according to an example method for posture state detection. A posture state cone may be centered about a posture state reference coordinate vector that corresponds to a particular posture state. In the examples of FIGS. 8A and 8B, the posture sensor 87 of IMD 14 or IMD 26 may include a three-axis accelerometer that provides data indicating the posture state of patient 12, to sense posture vectors. While the sensed posture data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture sensor parameter value from two axes of posture sensor 87 may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture vector is within an applicable angle or distance of the reference coordinate vector, or if the sensed posture vector and the reference coordinate vector produce a cosine value in a specified cosine range, then posture vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the output of posture sensor 87 to determine a sensed coordinate vector and identify the current posture of patient 12 by identifying which cone the sensed coordinated vector resides. For example, if the output of posture sensor 87 defines a sensed coordinate vector that falls within lying front cone 144, IMD 14 determines that patient 12 is lying down on their chest. IMD 14 may store this posture information as a determined posture state or as posture sensor data from the posture sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture sensor indicates that patient 12 is in upright cone 142, IMD 14 would not detect that patient 12 has entered a new posture cone until the output of posture sensor 87 indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which posture sensor data from posture sensor 87 is placed in relation to the posture cones. Posture state space 152 is substantially similar to posture state area 140 of FIG. 8A. However, the posture sensor data derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

As described above, in some examples, an offset signal shift and/or offset signal drift may be present in the output signal of a posture sensor such as an accelerometer. For example, for a 3-axis accelerometer sensor, offset shift/drift may be present in the output signal for one, two, or all three axes of the accelerometer sensor.

FIGS. 9A-D are conceptual diagrams illustrating example posture vectors 182, 184 within 3-dimensional posture state space 180. For purposes of illustration, the examples of FIG. 9A-D are described with regard to IMD 14 which utilizes a 3-axis accelerometer for posture sensor 87 that generates output signals for each of x, y, and z axis for measuring acceleration force in units of centi-G's (cG). However, other device and sensor configurations are contemplated.

As labeled in FIGS. 9A-D, the positive direction of the y-axis of the accelerometer sensor is aligned with the upright reference vector, i.e., V(Upright Ref), used by processor 80 as the reference vector for the upright posture state of patient 12. In the example of FIGS. 9A-9D, the upright vector is defined by signal output of [0,100,0] cG for the x, y, and z axis, respectfully, generated by posture sensor 87. Similarly, the lying front reference vector, i.e., V(Lying Front Ref) and lying back reference vector, i.e., V(Lying Back Ref) are aligned with the negative and the positive directions, respectively, of the z-axis of the accelerometer sensor. The lying front reference vector may be defined by signal output of [0,0,-100] cG for the x, y, and z axis generated by posture sensor 87, and the lying back reference vector may be defined by signal output of [0,0,100] cG for the x, y, and z axis. The lying left reference vector, i.e., V(Lying Left Ref) is aligned with the negative direction of the x-axis of the accelerometer sensor, and may be defined by a signal output of [-100,0,0] cG for the x, y, and z axis generated by posture sensor 87. The lying right reference vector is not shown in FIGS. 9A-D.

Within posture state space 180 of FIGS. 9A-D, first posture vector 182 represents a vector determined by IMD 14 based on posture sensor data generated by posture sensor 87 of posture state module 86 when an offset shift/drift in not present (or not present in any substantial amount) in the signal output of posture sensor 87. Conversely, second posture vector 184 represents a vector determined by IMD 14 based on posture sensor data generated by posture sensor 87 of posture state module 86 when an offset shift/drift is present in the signal output of posture sensor 87. More specifically, in the case of second posture vector 184, an offset shift of +40 cG is present in the z-axis signal of posture sensor 87 with substantially no offset shift/drift present in x-axis or y-axis signal. To illustrate the influence that offset signal shift/drift may have on the posture sensor data generated by posture sensor 87, especially with regard to the use of such data for posture detection, first and second posture vectors 182, 184 are shown simultaneously within posture state space 180 in FIGS. 9B-9D, despite the fact that such posture sensor data would not be generated simultaneously by posture sensor 87 but rather at different points in time, e.g., a time when offset shift/drift is present and a time when offset shift/drift is not present in the signal output.

Figure 9A:
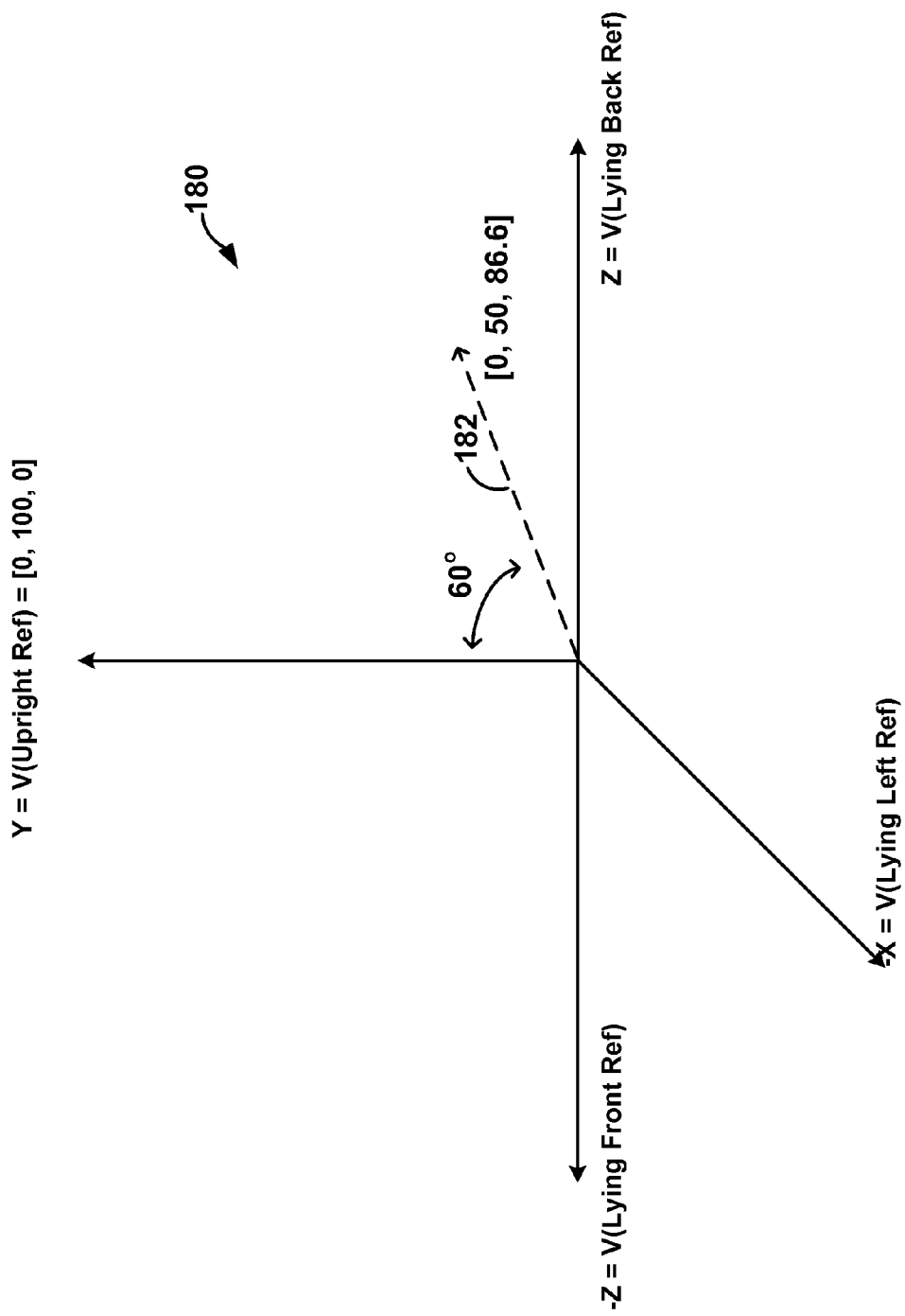
FIGS. 9A-9D are conceptual diagrams illustrating example sensed posture sensor data within example posture state space.

In FIG. 9A, processor 80 of IMD 14 determines first posture vector 182 based on a posture sensor signal output of [0,50,86.6] cG within posture state space of 180. Such a sensor signal may be generated by posture sensor 87 when patient 12 reclines back along the z-axis to approximately 60 degrees from the virtual upright reference vector. Processor 80 may employ Equation 1 to determine the angle of first vector 182 from the virtual upright reference vector:

$$\Theta_{calc} = \cos^{-1}\left(\frac{x1*x2 + y1*y2 + z1*z2}{\sqrt{x1^2 + y1^2 + z1^2} * \sqrt{x2^2 + y2^2 + z2^2}}\right) \quad (1)$$

where x1, y1, and z1 are the values of the upright reference vector along the x, y, and z axis, respectively, and where x2, y2, and z2 are the sensor output values along the x, y, and z axis, respectively, when patients occupies the reclined posture state corresponding to first posture vector 184. The magnitude of first posture vector 182 determined by processor 80 of IMD 14 based on the output of [0,50,86.6] cG is approximately 100 cG. Processor 80 may employ Equation 2 to determine the magnitude of a vector, V(mag), as:

$$V(mag) = (V_x^2 + V_y^2 + V_z^2)^{0.5} \quad (2)$$

where $V_x$ is the signal value along the x-axis, $V_y$ is the signal value along the y-axis, and $V_z$ is the signal value along the z-axis.

Figure 9B:
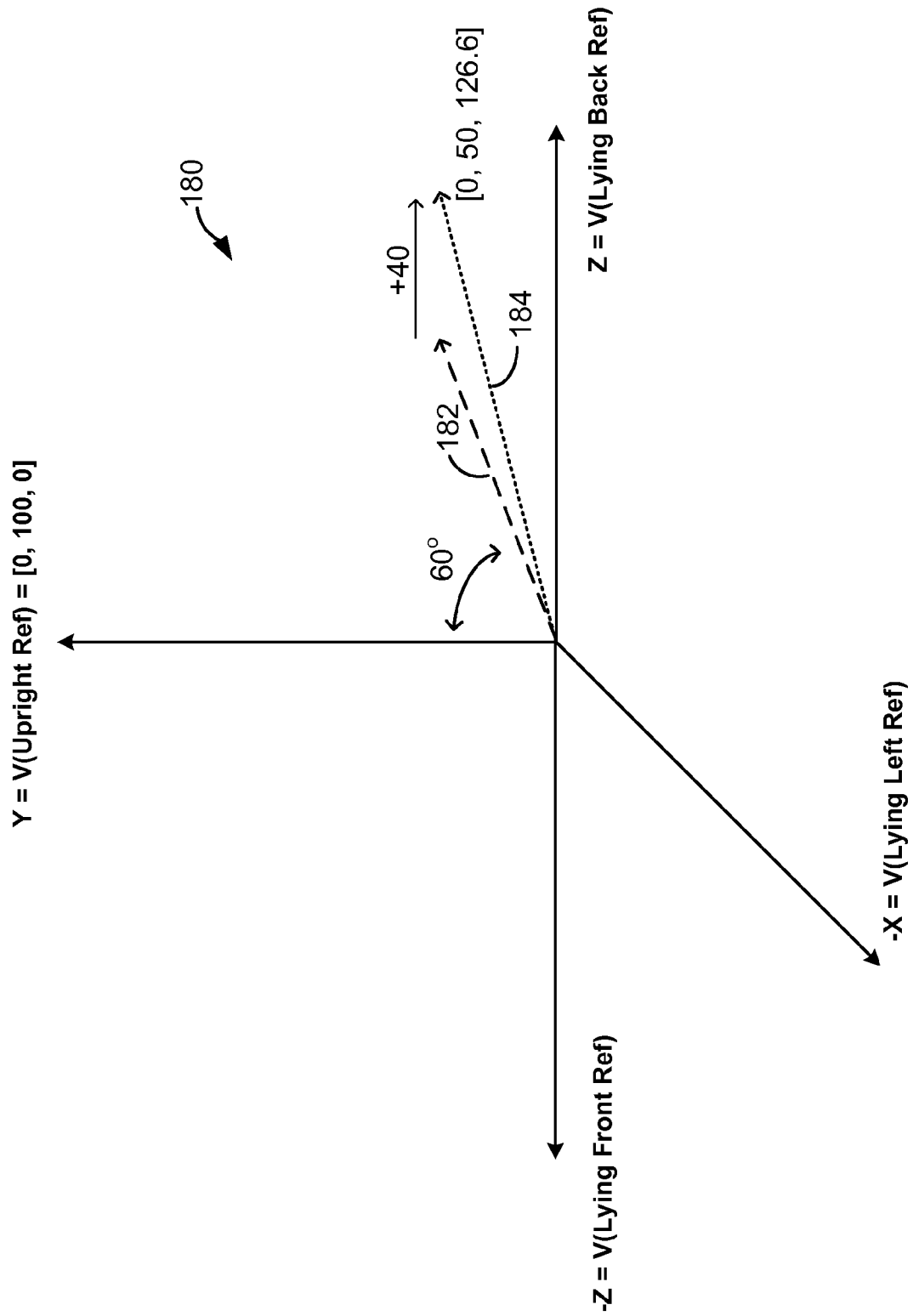

In FIG. 9B, first posture vector 182 is shown within posture state space 180 in substantially the same position as that in FIG. 9A. Second posture vector 184 is also shown in FIG. 9B. Second posture vector 184 may be determined by processor 80 of IMD 14 based on the posture sensor signal output generated when patient 12 occupies substantially the same actual posture state as that of first posture vector 182. However, unlike that of first posture vector 182, IMD 14 determines second posture vector 184 using posture sensor data generated by posture sensor 87 when a +40 cG offset shift is present in the z-axis signal. Because of the offset shift, in FIG. 9B, processor 80 determines the second posture vector based on a posture sensor output of [0,50,126.6] cG rather than a sensor output of [0,50,86.6] cG. In such an scenario, IMD 14 may detect that patient 12 has reclined along the z-axis to approximately 68.5 degrees from the virtual upright reference vector (e.g., using Equation 1) despite the fact that patient 12 maintains substantially the same actual posture state. In addition to detecting a different angle relative to the virtual upright reference vector, processor 80 of IMD 14 may determine that the magnitude of second posture vector 184 is approximately 136 cG compared to that of approximately 100 cG determined for first posture vector 182. Again, processor 80 may employ Equation 2 to determine the magnitude of first and second vectors 182, 184.

Figure 9C:
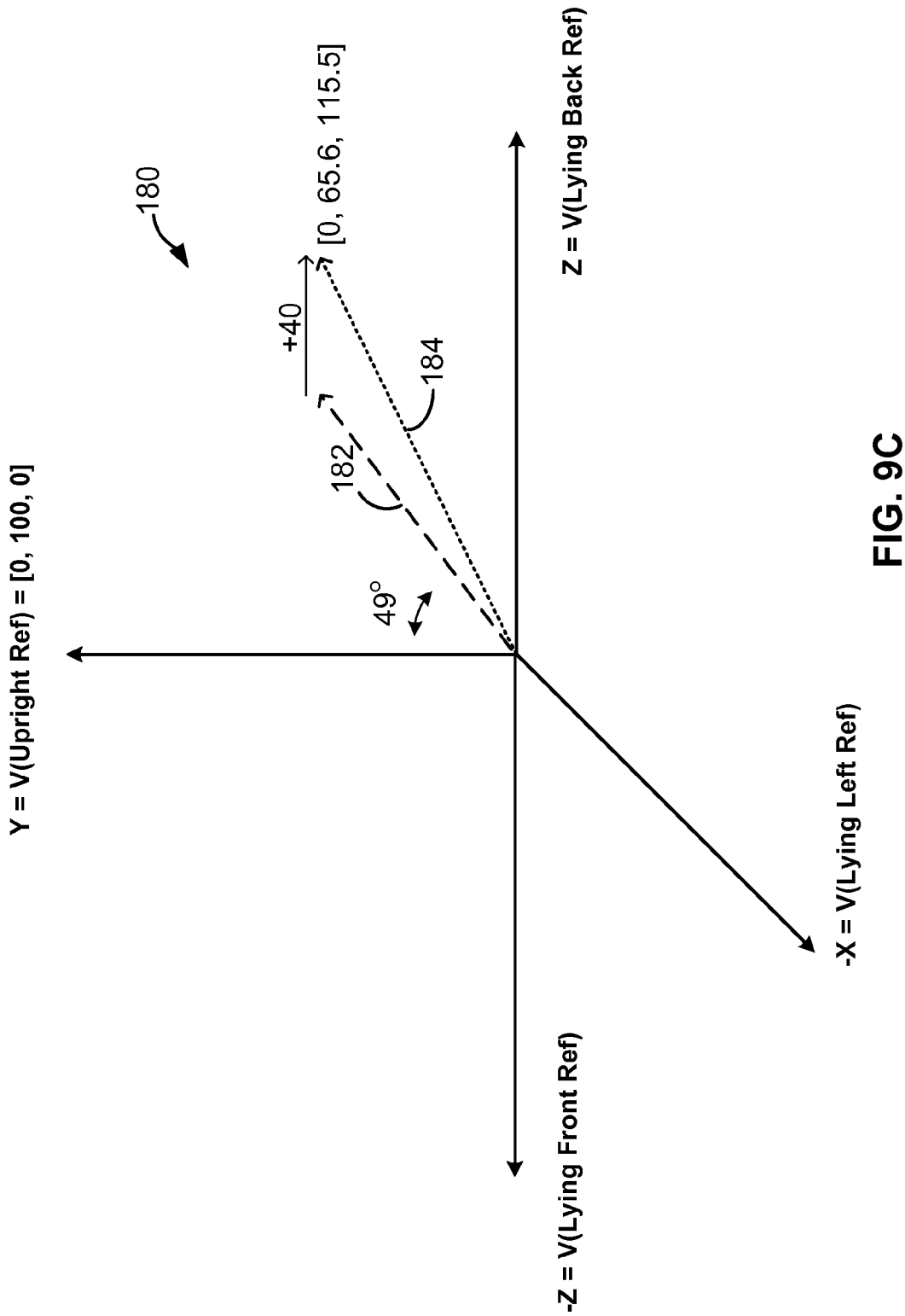

In FIG. 9C, processor 80 of IMD 14 determines first posture vector 182 based on a posture sensor signal output of [0,65.6,75.5] cG within posture state space of 180. Such a sensor signal may be generated by posture sensor 87 when patient 12 reclines back along the z-axis to approximately 49 degrees from the virtual upright reference vector. Using the posture sensor signal output of [0,65.6,75.5] cG, processor 80 may determine that first posture vector 182 has a magnitude of approximately 100 cG, which is approximately equal to that of the magnitude of first posture vector 182 shown in FIGS. 9A and 9B.

In FIG. 9C, processor 80 of IMD 14 determines second posture vector 184 based on the posture sensor signal output generated when patient 12 occupies substantially the same actual posture state as that of first posture vector 182 as shown in FIG. 9C. However, unlike that of first posture vector 182, IMD 14 determines second posture vector 184 using posture sensor data generated by posture sensor 87 when a +40 cG offset shift is present in the z-axis signal. Because of the offset shift, in FIG. 9C, processor 80 determines second posture vector 184 based on a posture sensor output of [0,65.6,115.5] cG rather than a sensor output of [0,65.6,75.5] cG. In such an scenario, IMD 14 may detect that patient 12 has reclined along the z-axis to approximately 60.4 degrees from the upright reference vector rather than approximately 49 degrees despite the fact that patient 12 maintains substantially the same actual posture state. In addition to detecting a different angle relative to the virtual upright reference vector, processor 80 may determine that the magnitude of second posture vector 184 is approximately 136.1 cG compared to that of approximately 100 cG for first posture vector 182.

Figure 9D:
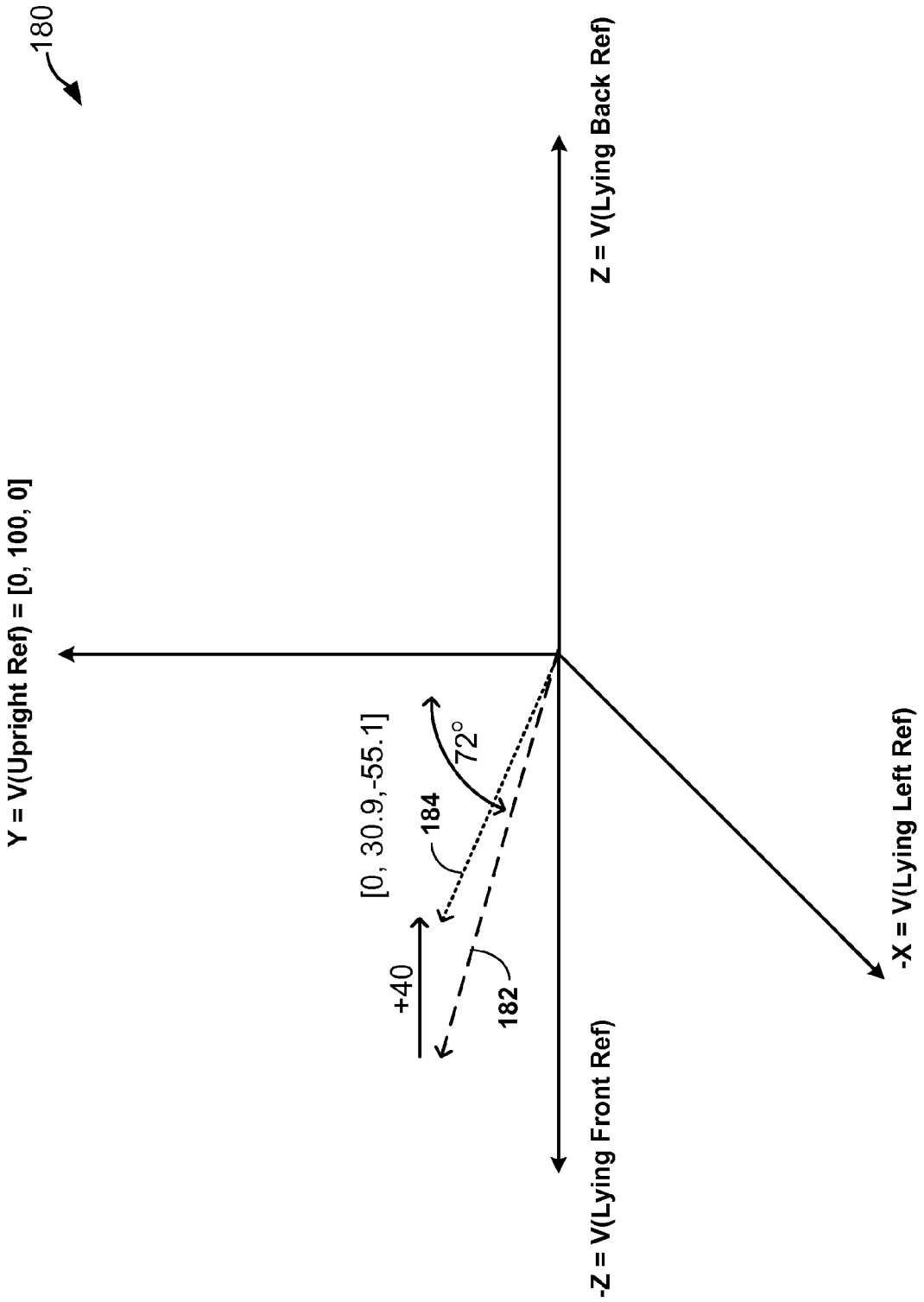

In FIG. 9D, processor 80 determines first posture vector 182 based on a posture sensor signal output of [0,30.9,−95.1] cG within posture state space of 180. Such a sensor signal may be generated by posture sensor 87 when patient 12 leans forward along the z-axis to approximately 72 degrees from the virtual upright reference vector. Using the posture sensor signal output of [0,30.9,−95.1] cG, processor 80 may determine that first posture vector 182 has a magnitude of approximately 100 cG, which is approximately equal to that of the magnitude of first posture vector 182 shown in FIGS. 9A-C.

In FIG. 9D, processor 80 determines second posture vector 184 based on the posture sensor signal output generated when patient 12 occupies substantially the same actual posture state as that of first posture vector 182 as shown in FIG. 9D. However, unlike that of first posture vector 182, IMD 14 determines second posture vector 184 using posture sensor data generated by posture sensor 87 when a +40 cG offset shift is present in the z-axis signal. Because of the offset shift, in FIG. 9C, processor 80 determines second posture vector 184 based on a posture sensor output of [0,30.9,−55.1] cG rather than a sensor output of [0,30.9,−95.1]. In such an scenario, IMD 14 may detect that patient 12 has leaned forward along the z-axis to approximately 60.7 degrees from the virtual upright reference vector rather than approximately 72 degrees despite the fact that patient 12 maintains substantially the same actual posture state. In addition detecting a different angle relative to the virtual upright reference vector, processor 80 may determine that the magnitude of second posture vector 184 is approximately 63.2 compared to that of approximately 100 cG for first posture vector 182.

As illustrated by FIGS. 9A-D, the presence of an offset shift/drift in the output signal of postures sensor 87 can influence the position of a posture vector in posture state space 180 detected by IMD 14 using the postures sensor data from posture sensor 87. In some instances, the presence of an offset shift/drift may inhibit the ability of IMD 14 to detect the actual posture state of patient 12 using the posture sensor generated by posture sensor 87. For example, when a +40 cG offset shift is present as in FIGS. 9A-D, in a scenario in which the upper boundary of a postures cone that defines the zone within posture space 180 for the "lying back" posture state is approximately 60 degrees from the virtual upright vector on the positive z-axis, patient 12 would need only actually lean back approximately 49 degrees from the virtual upright vector toward the positive z-axis for processor 80 of IMD 14 to detect that patient 12 is approximately at the 60 degree upper boundary of the lying back posture cone based on the posture state data generated by posture sensor 87 at that point in time. In this manner, the presence of the offset signal drift in essence moves the upper boundary of the lying back posture cone about 11 degrees to approximately 49 degrees from the upright vector along the positive z-axis. When patient 12 actually leans back approximately 60 degrees, processor 80 of IMD 14 detects that patient 12 is beyond the upper boundary of the lying posture cone but instead is leaning back approximately 68.5 degrees from the virtual upright vector.

Similarly, in the presence of the same +40 cG offset shift, for a scenario in which the upper boundary of a postures cone that defines the zone within posture space 180 for the "lying front" posture state is approximately 60 degrees from the virtual upright vector on the negative z-axis, patient 12 would need to actually lean forward approximately 72 degrees from the virtual upright vector toward the positive z-axis for IMD 14 to detect that patient 12 is approximately at the 60 degree upper boundary of the lying front posture cone based on the posture state data generated by posture sensor 87 at that point in time. In this manner, the presence of the offset signal drift in essence moves the upper boundary of the lying front posture cone about 12 degrees to approximately 72 degrees from the upright vector along the positive z-axis.

Figure 10B:
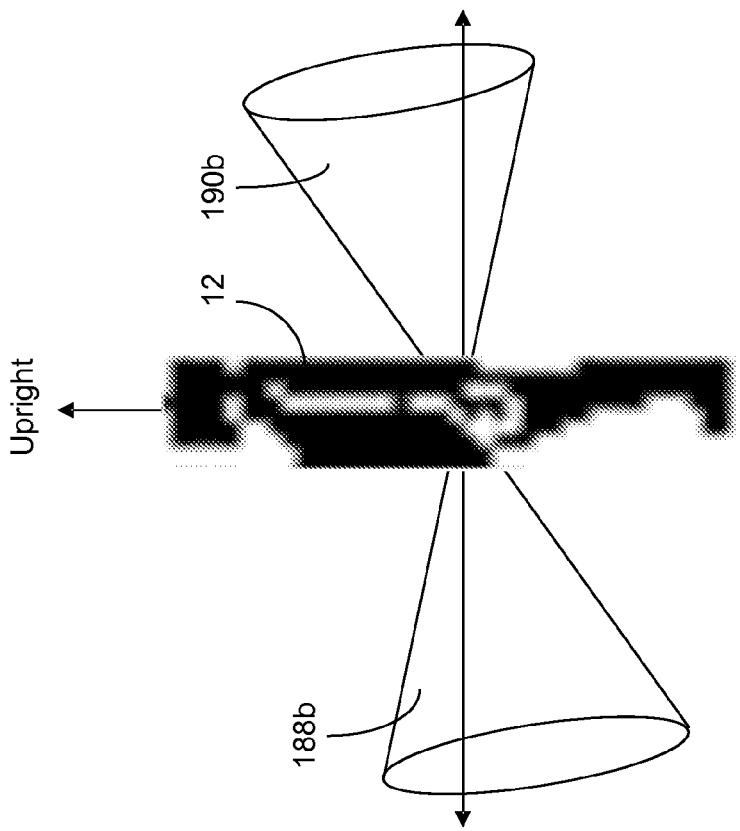
FIGS. 10A and 10B are conceptual diagrams illustrating an example patient from a side view in an example posture state space including example posture state cones.
Figure 10A:
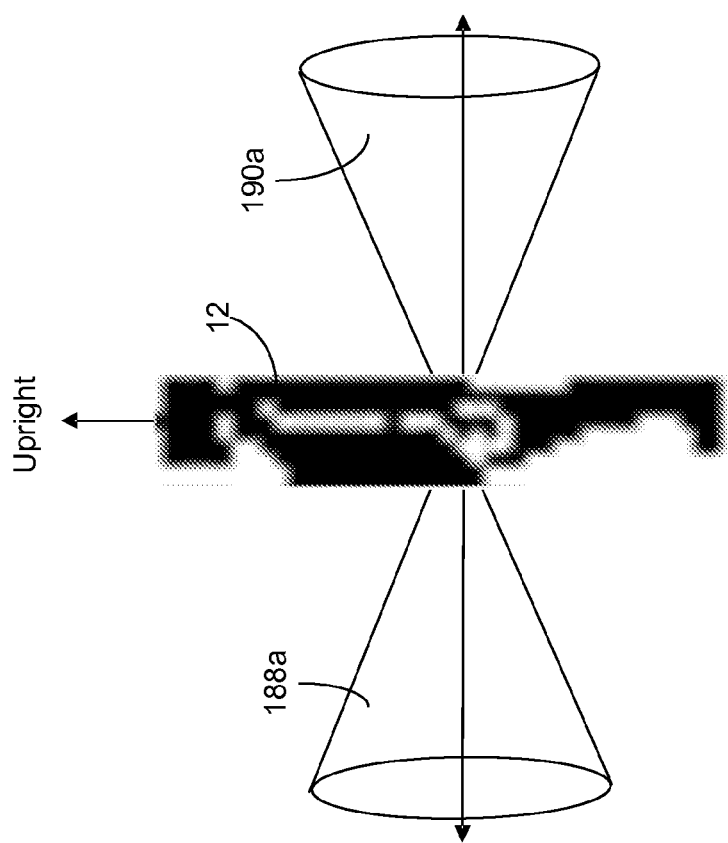
Figure 11B:
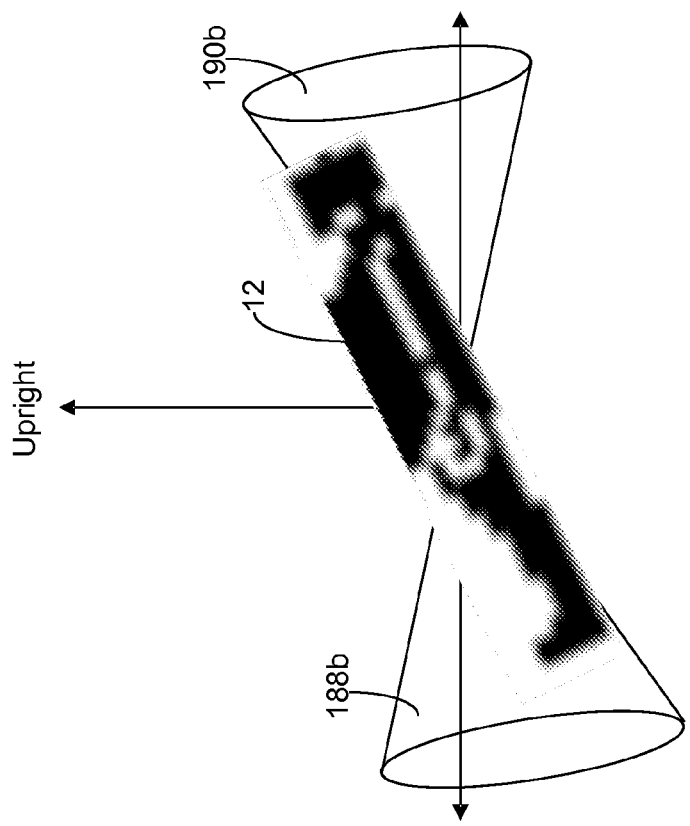
FIGS. 11A and 11B are conceptual diagrams illustrating an example patient from a side view in an example posture state space including example posture state cones.
Figure 11A:
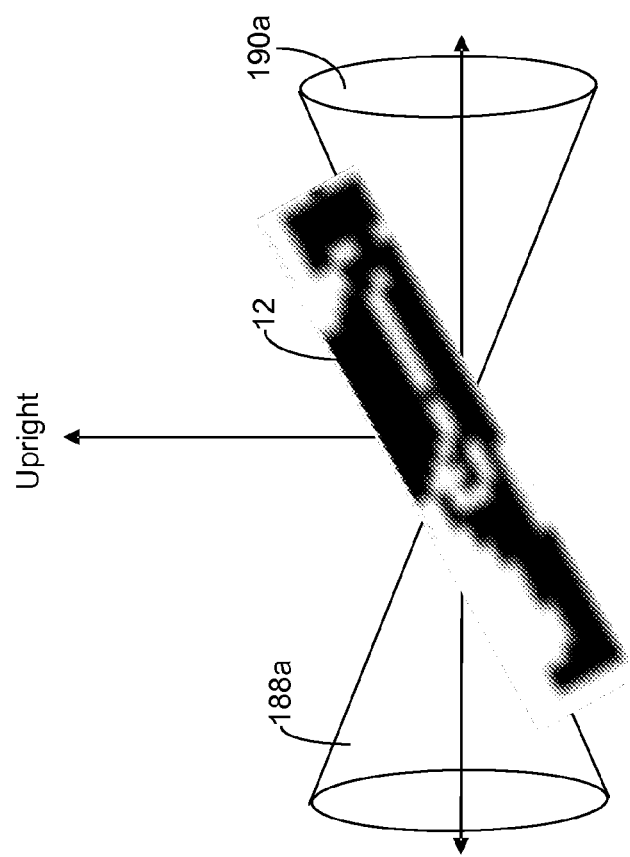

FIGS. 10A, 10B, 11A and 11B are conceptual diagrams illustrating patient 12 from a side view to demonstrate the influence that the presence of offset shift/drift in the signal output generated can have on posture state detection. FIGS. 10A and 11A show the orientation of lying front posture cone 188a and lying back posture cone 190a for examples in which an offset shift is not present in any substantial amount in the output signal generated by posture sensor 87, as was the case for the posture sensor data used to determine first posture vector 182 in FIGS. 9A-D. Conversely, FIGS. 10B and 11B show the orientation of lying front posture cone 188b and lying back posture cone 190b for examples in which an offset shift is present in the output signal generated by posture sensor 87, e.g., as was the case for the posture sensor data used to determine second posture vector 184 in FIGS. 9B-D.

As shown, the presence of the offset shift in the signal output of posture sensor in FIGS. 10B and 11B effectively skews lying back posture cone 190b toward the upright vector and lying front posture cone away from the upright vector. In FIGS. 10A and 10B, patient 12 occupies an example upright posture state and IMD 14 may detect that patient is in an upright posture state (or at least not within either lying front posture cones 188a, 188b or lying back posture cones 190a, 190b) based on the posture sensor data generated by posture sensor in each instance. However, in FIGS. 11A and 11B, patient 12 is reclined back from the upright vector. In the example of FIG. 11A, processor 80 of IMD 14 may detect that patient 12 is still outside the lying back posture cone 190a and lying front posture cone 188a based on the posture sensor data generated by posture sensor 87. Conversely, in the example of FIG. 11B, processor 80 of IMD 14 may detect that patient 12 is within lying back posture cone 190a. As such, IMD 14 may detect that patient 12 is not in the lying back posture state in the example of FIG. 11A but detect that patient 12 is in the lying back posture state in the example of FIG. 11B even though patient 12 occupies substantially the same reclined position in both FIGS. 11A and 11B. In cases in which IMD 14 delivers therapy to patient 12 according to the detected posture state of patient 12, IMD 14 may deliver a different therapy to patient 12 in the scenarios of FIG. 11A and FIG. 11B based on the different posture states that may be detected by IMD 14 in each scenario. As illustrated by the above, while the posture sensor data from a posture sensor may be indicative of a posture state of patient 12 (e.g., when analyzed relative to posture state reference data), when offset shift/drift is present in the output of posture sensor 87, such data may not accurately reflect the actual posture state of patient 12 in some instances.

In accordance with one or more examples of the present disclosure, IMD 14 or other processing device may be configured to detect the presence of an offset signal shift/drift in the output signal(s) generated by posture sensor 87. For example, processor 80 of IMD 14 may detect the presence of offset shift/drift in the output signal(s) generated by posture sensor 87 by comparing posture sensor data generated by posture state sensor 87, e.g., when patient 12 occupies one or more specific posture states to reference postures sensor data. In some instances, upon detection of the presence of an offset shift/drift in the output signal(s) generated by posture sensor 87, processor 80 may determine an appropriate offset correction to be applied to the posture sensor data to account for the offset shift/drift identified in the signal output of posture sensor 87.

Figure 12:
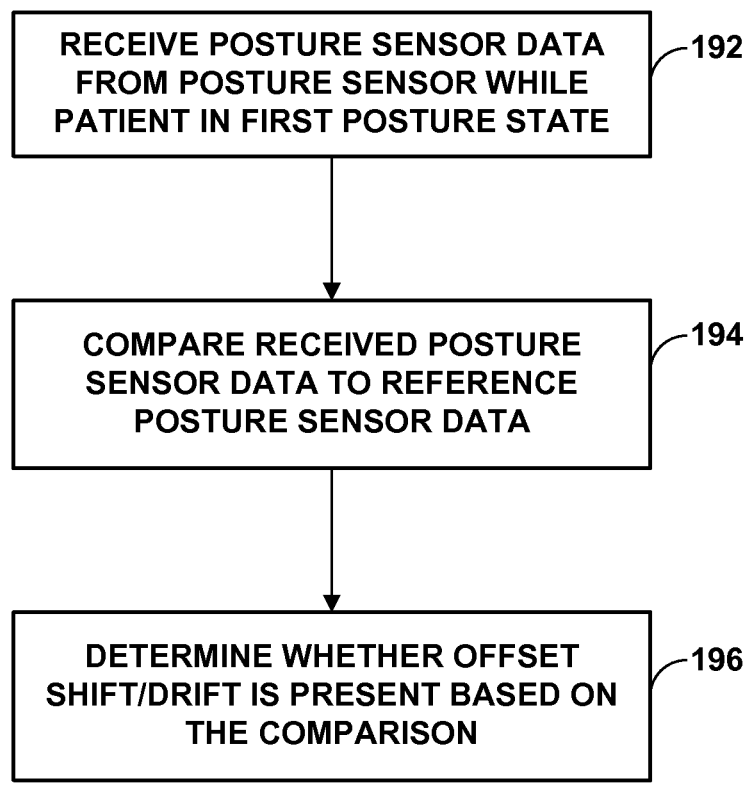
FIG. 12 is a flow diagram illustrating an example technique for detecting the presence of offset signal shift and/or offset signal drift in the output of an example posture sensor.

FIG. 12 is a flow diagram illustrating an example technique for detecting the presence of signal offset shift/drift in the output signal(s) of a posture sensor. For ease of description, the example technique of FIG. 12, as well as the examples of FIGS. 13-16 are described with regard to patient 12 and therapy system 10 including IMD 14 and external programmer 20. Also, as before, the following examples are described for examples in which posture sensor 87 of IMD 14 includes a three-axis accelerometer that generates signal outputs for each of the x, y, and z axes that defines at least in part posture sensor data used by processor 80 of IMD 14 to detect the posture state of patient 12. However, devices and configurations other than that described are contemplated. For example, IMD 14 may include multiple, single or multi-axis accelerometer devices or other posture sensors to define posture state data that may be analyzed by processor 80 to determine the posture state of patient 12. The following example techniques are primarily described as being performed by IMD 14. However, in other examples, all or portions of the example techniques may be carried out by other devices, such as, e.g., external programmer 30 (FIG. 1) or other external computing device, in addition to or as an alternative to IMD 14.

In the example of FIG. 12, processor 80 of IMD 14 receives postures sensor data from posture sensor 87 when patient 12 occupies a first posture state (e.g., upright, lying back, lying front, lying left, or lying right)(192). In this case, patient 12 may be known to occupy the first posture state when the posture sensor data is received. Patient 12 may be guided by a clinician to the first posture state, e.g., for the dedicated purpose of checking for offset shift/drift, and/or patient 12 may be instructed to occupy the first posture state, e.g., via user interface 106. Processor 80 then compares the posture sensor data generated when patient 12 is in the first posture state to reference posture sensor data, which may be stored in memory 82 of IMD 14 and/or memory 108 of programmer 20 (194). In some examples, the reference posture sensor data may be associated with the first posture state and may be unique to the first posture state or may be reference posture sensor data used for comparison to received posture sensor data for a plurality of different posture states. Accordingly, the reference posture sensor data compared to the received posture sensor data may be specific to the first posture state or may be generally applicable to posture sensor data received from posture sensor 87 regardless of the posture state of patient 12.

Based on the comparison of the posture sensor data generated by posture sensor 87 to reference posture sensor data, processor 80 may determine whether a signal offset shift/drift is present in the output of posture sensor 87 (196). In some examples, upon detection of offset shift/drift, processor 80 and/or another processor device may carry out steps to correcting for the presence of the offset shift/drift in the output of posture sensor 87 for use in detecting the posture state of patient 12. Additionally or alternatively, processor 80 may generate an alert or other indication that is communicated to a user, such as, patient 12 or a clinician. Based on the indication, the user may verify the detection and/or determine what, if any, steps should be taken to correct the offset shift/drift in the output of posture sensor 87.

As described above, posture sensor data analyzed by processor 80 may include output signal values sampled from each of the x, y, and z, axis signals of posture sensor 87. For example, in the case of first posture vector 182 in FIG. 9A, the posture sensor data may include values of zero cGs, 50 cGs, and 86.6 cGs for the x, y, and z-axis, respectively. Processor 80 may determine values for each of the x, y, and z axis from a single sample of the output of posture sensor 87 or a plurality of samples, e.g., an average of multiple samples values, of the output of posture sensor 87. In some examples, the posture sensor data may include a magnitude of the coordinate vector determined based on the values for each of the x, y, and z-axis, which may be determined by processor 80, for example, using Equation 2. For ease of description, such a vector may be referred to in this disclosure in some instances as a posture vector. As such, the posture sensor data may include values for each of the x, y, and z-axis and/or one or more magnitudes of the posture vector derived from x, y, and z-axis values. Processor 80 may store posture state data used to identify whether or not an offset shift/drift is present in memory 82, memory 108 (FIG. 6), or memory of other device.

Based on the actual posture sensor signal output of posture sensor 87 received while patient 12 occupies the first posture state (192), processor 80 may determine posture sensor data for the first posture state based on the output of posture sensor 87. For example, processor may determine an average value for each of the x, y, and z-axis signals generated by posture sensor 87 at one or more instances during all or a portion of the time that patient 12 occupies the first posture state. Additionally or alternatively, processor 80 may determine a magnitude of the posture vector based on the value(s) of each of the x, y, and z-axis signals generated during the time that patient occupies the first posture state. Other metrics which are determined based on the output generated by posture sensor 87 and that may be used by processor 80 to identify the presence of offset shift/drift in the output of posture sensor 87 via one or more examples described herein are also contemplated.

The sensor output generated by posture sensor 87 when patient 12 is in the first posture state (192) may or may not include offset shift/drift in one or more of the output signals (one or more of the x, y, and z-axis signals) of posture sensor 87. To determine whether an offset shift/drift is present in one or more of the output signals, processor 80 may compare the posture sensor data received when patient 12 occupies the first posture state to reference posture sensor data (194). The reference postures sensor data may be stored in memory 82 and/or memory 108.

In some examples, the reference posture sensor data compared to the received posture sensor data (194) may include posture sensor data representative of posture sensor data generated by posture sensor 87 when patient 12 occupies the first posture state at a time when substantially no offset shift/drift is present or at least present only in an acceptable amount. In such an instance, the comparison of the reference posture sensor data to the posture sensor data determined based on the posture sensor output generated when patient 12 occupies the first posture state may include processor 80 determining the differences between the respective posture sensor data. If processor 80 determines that one or more differences exist between the reference posture sensor data and the posture sensor data determined from the output of posture sensor 87 (192), processor 80 may detect that an offset shift/drift in present in one or more of the output signal(s) generated by posture sensor. In some examples, processor 80 may detect that an offset shift/drift is present in the output of posture sensor 80 if the difference between the respective posture sensor data is greater than a threshold value. The threshold value may be preprogrammed, e.g., by a clinician, and stored in memory 82. In some examples, the threshold value may correspond to the variability inherent in the output signal(s) generated by posture sensor 87, e.g., due to varying gain error on each axis. Conversely, if processor 80 determines that there is substantially no difference between the baseline posture sensor data and the posture sensor data determined from the output of posture sensor 87 (192), then processor 80 may determine that offset shift/drift is not present or not present in any substantial amount in the output signal(s) generated by posture sensor 87. In some examples, processor 80 may repeat the example technique of FIG. 12 for a plurality of posture states of patient 12 rather than only a first posture state. For example, such a process may be carried out for at least three posture states of patient 12 in the case of a posture sensor including outputs along each of an x, y, and z axis. In some examples, the reference posture sensor date includes a "typical" vector magnitude that is compared to the current vector magnitude for each of the at least three posture states. In some examples, the three posture states of patient 12 may be approximately orthogonal to each other within the three-dimensional posture state space defined by the x, y, and z axis outputs. In this manner, the posture sensor data for at least one of the three posture states of patient may be influenced by an offset shift/drift in the output of posture sensor 87 when present to a degree that may be result in a difference between the posture sensor data and reference posture sensor data.

The reference posture sensor data may be defined by a value or range of values for each of one or more parameters of posture sensor data. In some examples, the range may be defined by a parameter value in combination with value range above and below that parameter value that defines the overall range of the baseline parameter value. For purposes of comparison, the reference posture sensor data may be defined in terms of parameters that are substantially the same as those parameters used to define the posture sensor data determined by processor 80 based on the output of posture sensor 87 (192). For example, if the reference posture sensor data for the first posture state is defined in part by a value or range of values for the magnitude of a vector representative of posture sensor output, processor 80 may determine the magnitude of the posture vector (e.g., using Equation 2) from the output of posture sensor 87 along the x, y, and z-axis when patient 12 occupies the first posture state (192). Similarly, if the reference posture sensor data for the first posture state is defined in part by a value or range of values for output of posture sensor along each axis, then processor 80 may determine the value from the output of posture sensor along each axis when patient 12 occupies the first posture state (192).

In this manner, processor 80 may readily compare the determined posture vector magnitude value to the value or range of values for the magnitude defining the reference magnitude defined for the first posture state. The reference magnitude may be value unique to the first posture state of the patient or a value applicable to multiple patient posture states, e.g., substantially all patient posture states. Likewise, if the reference posture sensor data is defined in part by a value or range of values for the output signal of each of the individual axis of posture sensor 87, the processor 80 may determine a value for the output signal of each of the individual axis of posture sensor 87 when patient 12 occupies the first posture state (192). Again, in this manner, processor 80 may readily compare the respective posture sensor data, e.g., to determine whether or not one or more differences exist that may be indicative of the presence of offset shift/drift in the output of posture sensor 87.

In some examples, processor 80 may evaluate the output of posture sensor 87 for the presence of offset shift/drift for only a single posture state, as shown in FIG. 12. In other examples, processor 80 may be configured to repeat the example technique of FIG. 12 for a plurality of posture states. For example, processor 80 may evaluate the output of posture sensor 87 according to the example of FIG. 12 for two or more of an upright posture state, lying back posture state, lying front posture state, lying right posture state, and lying left posture state. As described above, in some example, processor 80 may evaluate the output of posture sensor 87 according to the example of FIG. 12 for at least three posture states that are approximately orthogonal to each other (e.g., upright, lying back or front, and lying right or left posture states). In the case of a posture sensor including outputs along two-axes rather than three, processor 80 may evaluate the output of posture sensor 87 according to the example of FIG. 12 for at least two posture states that are approximately orthogonal to each other within the two-dimensional posture space of the posture sensor output. In each case, the multiple posture states may be distributed throughout the posture state area or space of the posture sensor output.

Reference posture sensor data may be defined for each of the respective posture states, and may be stored, e.g., in memory 82 or memory 108 of programmer 20. In some examples, the reference posture sensor data associated with each individual posture state may be different from one another (e.g., for examples in which values for the output signal of each individual axis of posture sensor 87 are define the baseline posture sensor data), while in other examples, the reference values for two or more different posture states may be substantially the same as one another (e.g., for example in which values for the magnitude of a posture vector derived from the output of each axis of posture sensor define the baseline posture state data).

In some examples in which processor 80 is configured to perform the technique of FIG. 12 for a plurality of posture states, processor 80 may cycle through some or all of the plurality of posture states regardless of the outcome of the posture sensor data comparison. In other examples, the progression through respective posture states of patient 12 may depend on the outcome of the comparison of posture sensor data for a posture state to reference posture sensor data for that posture state. For example, processor 80 may initially perform the example technique of FIG. 12 for a first posture state of patient. If the comparison of the posture sensor data for the first posture state to the reference posture sensor data is indicative of the presence of offset shift/drift, processor 80 may repeat the process for a second patient posture state to determine if the presence of the offset shift drift is also indicated by the comparison of the posture sensor data for the second posture state to the reference posture sensor data, which may be substantially the same or different than the reference posture sensor data used for the first posture state. Conversely, if the comparison of the posture sensor data for the first posture state to the reference posture sensor data is not indicative of the presence of offset shift/drift, then processor 80 may end the detection process without proceeding to evaluate the sensor signal data for a subsequent posture state. In some examples, processor 80 may end the detection process only after posture sensor data for three posture states approximately orthogonal to each have been evaluated as shown in FIG. 12.

For each posture state occupied by patient 12, processor 80 may receive an indicator indicating that patient 12 is occupying (or will be occupying) a desired posture state. This indicator may be used to ensure that patient 12 is actually occupying the desired posture state when processor 80 analyses the output of posture sensor 87 for comparison of the posture sensor data to reference posture sensor data. Such an indicator may be communicated from a user to processor 80 via external programmer 20. In some examples, external programmer 20 may be used to instruct patient 12 to enter a desired posture state (e.g., an upright posture state) and then indicate to processor 80 of IMD 14 when patient actually occupies the desired posture state, e.g., based on the receipt of confirmation from patient 12 entered via user interface 106 (FIG. 6). In some examples, external programmer 20 may guide patient 12 through a sequence of posture states so that processor 80 may determine posture sensor data for each of a plurality of posture states and compare the determined posture sensor data to reference posture sensor data corresponding to the respective posture state, e.g., as shown in the example of FIG. 12. As described above, the reference posture sensor data may be substantially the same or different for each respective posture state.

In some examples, the reference posture sensor data may include baseline posture sensor data defined by actual sensor signal data generated by posture sensor 87 at some previous period of time. In some examples, baseline posture sensor data for a particular posture state may be defined by actual sensor signal data generated by posture sensor 87 at some previous period of time, e.g., when patient 12 occupied approximately the same posture state, e.g., in a clinic visit. The previous period of time during which the baseline posture sensor data is defined may generally correspond to a period of time when offset shift/drift was not present in the output of posture sensor 87 or was only present in a relatively insignificant and/or acceptable amount. Differences in posture sensor data sensed at a later time relative to the baseline posture sensor data may be attributed to the presence of offset shift/drift in the signal output of the posture sensor. In some examples, baseline posture sensor data determined based on the output of posture sensor 87 when patient 12 occupies one or a plurality of approximately orthogonal posture states may be used to define reference posture sensor data for one or more other posture states of patient 12, e.g., when the reference posture sensor data is defined by the "typical" magnitude, e.g., average magnitude, of the posture vectors derived from the output of each of the x, y, and z axis signals. An example technique for defining reference posture sensor data including baseline posture sensor data based on actual output of posture sensor 87 is described below with regard to FIG. 13.

Alternatively or additionally, the reference posture sensor data may be a predetermined by a user, such as, e.g., a clinician. For example, reference posture sensor data may be defined by a user based on or more values estimated or otherwise known to be representative of the actual posture sensor data for a posture state when substantially no offset shift/drift is present. In some examples, such posture sensor data may be defined by a manufacturer based on specification values for an accelerometer device or previous patient(s) in which substantially the same or similar posture sensor has been used. In some examples, the reference posture sensor data may be determine from sampling of the sensor signal prior to implantation of the IMD, e.g., during a trial stimulation period or during that manufacturing process of the IMD.

As the output signals for each axis of a multiple axis accelerometer can depend on the physical orientation of the accelerometer in a patient, the average magnitude of the posture vector derived from the signal values for each axis observed in other patients and/or otherwise defined for the particular accelerometer may be used as reference posture sensor data rather than output signal values for each individual axis. As an illustration, while the values along the x, y, and z-axis may vary for the first posture vector 182 in FIG. 9A-D, in each example the magnitude of first posture vector is approximately 100 cGs in each instance. In such an example, the reference posture sensor data associated with one or more of the posture states may be defined as a magnitude of approximately 100 cGs, and may be independent of the particular orientation of posture sensor 87 within patient 12. Such a reference magnitude may be determined based on actual posture sensor data generated by posture sensor 87 when patient 12 is in one or more posture states or may be determined prior to implantation, such as, e.g., during a trial stimulation period and/or during a testing phase of the manufacturing process of IMD 14.

Processor 80 (or other processing device) may analyze posture sensor data for offset shift/drift using one or more of the example techniques described herein on a substantially continuous or periodic basis. In some examples, processor 80 may automatically or semi-automatically (e.g., based on user confirmation of a request generated by processor 80 and communicated via external programmer 20) analyze posture sensor data to detect the presence of offset shift/drift in the output of posture sensor 87. Alternatively or additionally, processor 80 may analyze posture sensor data for offset shift/drift upon receipt of a user request, e.g., a user request communicated to IMD 14 via an external programming device 20. Processor 80 may analyze posture sensor data as described herein to detect the presence of offset shift/drift initially upon implantation of IMD 14 in patient 12, e.g., during an initial programming session. In such cases it may be necessary to use reference posture sensor data that is not defined based on actual posture sensor data measured for posture sensor 87 when implanted in patient 12. Rather, in such a case, one or more predefined values may be used to define the reference posture sensor data used for respective posture states. In some examples, posture sensor 87 may be evaluated prior to implantation of IMD 14, e.g., during a trial stimulation period when posture sensor 87 is worn externally to detect patient posture state, to prevent implantation of IMD 14 when posture sensor 87 is exhibiting offset shift/drift in one or more output signals. In some examples, e.g., when posture sensor 87 is the same sensor used for external trial stimulation as that which is implanted, reference posture sensor data defined during a trial stimulation period may be used identify offset shift/drift after IMD 14 has been implanted in patient 12 by way of comparison to posture sensor data generated after implantation, e.g., as measured during an initial programming session.

As will be described further below, if processor 80 determines that an offset shift/drift is present in the output of posture sensor 87, processor 80 may then generate an alert that may be communicated to a user, such as, e.g., patient 12 or a clinician, via external programmer 20 or other external device. In some examples, IMD 14 may suspend the delivery of posture responsive therapy to patient 12 or prevent the activation of posture responsive therapy delivery until the offset shift/drift detected by processor 80 is addressed or an override command is received from an authorized user such as a clinician.

Alternatively or additionally, if an offset shift/drift is detected in the output of posture sensor 87, processor 80 or the processor of another medical device may determine and apply an offset correction. The offset correction may be applied to the sensor signal data generated by posture sensor 87 to address the detected offset shift/drift. For example, the offset correction applied to the detection algorithm used by IMD 14 to detect the posture state of patient 12 based on the posture sensor data generated by posture sensor 87. The offset correction applied to the posture state detection algorithms may allow the IMD to account for presence of offset shift/drift in an accelerometer output signal such that the IMD may accurately detect the posture state of patient 12 based on the posture sensor data even with the offset shift/drift present in the output of posture sensor 87. An example technique for determining an offset correction for the output of posture sensor 87 is described further below with regard to FIG. 15. However, other example techniques are contemplated.

Figure 13:
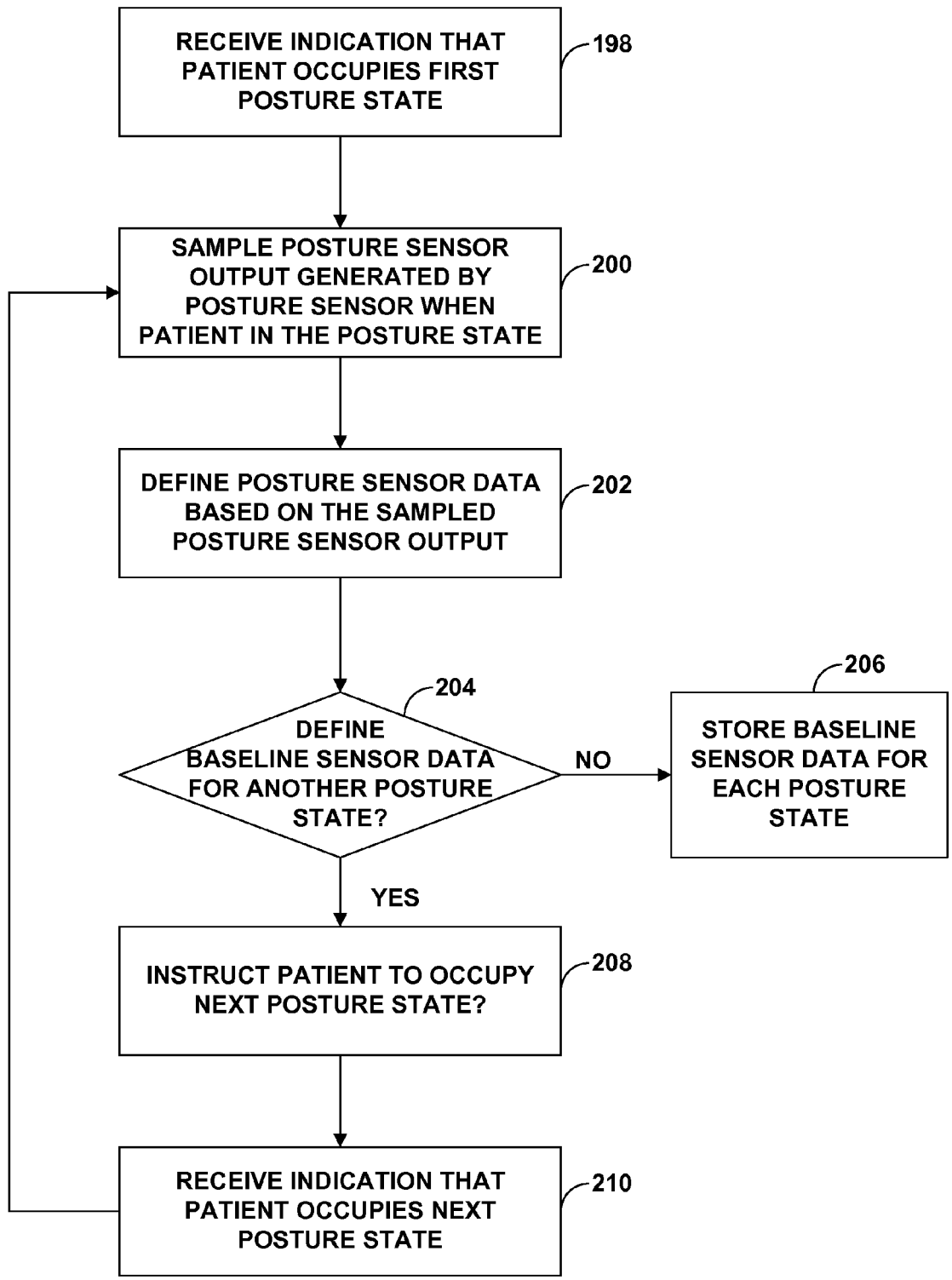
FIG. 13 is a flow diagram illustrating an example technique for defining reference posture sensor data for one or more posture states.

FIG. 13 is a flow diagram illustrating an example technique for defining reference posture sensor data for one or more posture states of patient 12. As described above, in some examples, the reference posture sensor data used by processor 80 to detect the presence of offset shift/drift in the output of posture sensor 87 may include baseline posture sensor data defined based on actual posture sensor data generated at some prior period of time by posture sensor 87.

Initially, to define reference posture sensor data for a first posture state, processor 80 may receive an indication, e.g., from external programmer 20, indicating that patient 12 actually occupies or will soon be occupying a first posture state, such as, e.g., an upright posture state. The indicator may be communicated based on input provided to external programmer 20 via user interface 106 (FIG. 6). As described above, in this manner, processor 80 may confirm that patient 12 actually occupies the first posture state for which reference posture state data will be defined (198). In other examples, processor 80 may not need to know the particular posture state occupied by patient 12, e.g., in cases in which a single posture vector magnitude is used to define reference posture sensor data for more than one or even substantially all posture states of patient 12.

Upon receipt of the indication from external programmer 20, processor 80 samples the output signals generated by posture sensor 87 when patient 12 occupies the first posture state (200). For example, processor 80 may sample the output for each of the x, y, and z-axis signals to determine one or more values of the output signal for each axis generated by posture sensor 87 when patient 12 occupies the first posture state. While processor 80 is sampling the output of posture sensor 87, patient 12 may be instructed to maintain a relatively static position to minimize the variation of the output of posture sensor 87.

Based on the sampled posture sensor signal values, processor 80 may define posture sensor data for the first posture state (202). For instances in which the reference posture sensor data includes values for each of the x, y, and z-axis, processor 80 may determine the average output value for each axis of the posture sensor based on a plurality of values sampled during the time period that patient 12 occupies the first posture state. Additionally or alternatively, processor 80 may determine a magnitude of the posture vector that defines the baseline posture sensor data for the first posture state using sampled output values while patient occupies the first posture state per Equation 2 above.

After defining the baseline posture state data for the first posture state, processor 80 may determine whether or not to define a baseline posture state for another posture state of patient 12 (204). The number of posture states that processor 80 defines baseline posture state information may be a preprogrammed value stored in memory 82. In some examples, a clinician may be able to select the number of posture states, either during or in advance of the example process of FIG. 13. Regardless of how the number of posture states is selected, if processor 80 determines reference posture sensor data is to be defined for additional posture states, processor 80 may instruct patient 12 via external programmer 20 to occupy a posture state other than that of the first posture state (208). Subsequently, processor 80 may receive an indication that patient 12 is or will soon be occupying the next posture state (210), e.g., as described above for the indication received that patient 12 occupies the first posture state (198). As with the first posture state, processor 80 then samples the output signals generated by posture sensor 87 when patient 12 is occupying the next posture state (200), and then defines posture sensor data for the respective posture state based on the sampled output of posture sensor 87. Once reference posture sensor data has been defined for all the desired posture states of patient 12, processor 80 stores the reference posture sensor data with the associated posture in memory 82. In some examples, processor 80 may determine an average posture vector magnitude from multiple individual posture vector magnitudes determined based on the output of posture sensor 87 for a plurality of patient posture states to define a single baseline magnitude value that defines reference posture sensor data for more than one, e.g., substantially all, patient posture states. Processor 80 may access the reference posture sensor data for one or more of the posture states in memory 82 at a later time to detect whether offset shift/drift is present in the output of posture sensor 87, e.g., by way of comparison with posture sensor data from the output of posture 87 at that later time.

In some cases, the example technique of FIG. 13 may be performed during an initial programming session. In some examples, the described process may take place in conjunction with the initial orientation of posture sensor 87 to define all or a portion of posture state reference data used by processor 80 to detect the posture state of patient 12, e.g., when IMD 14 is active for delivery of posture responsive therapy to patient 12. In some cases, unique posture states of patient 12 may be defined specifically for use in evaluating the posture sensor for the presence of output shift/drift rather than for use by processor 80 during the delivery of posture responsive therapy.

Figure 14:
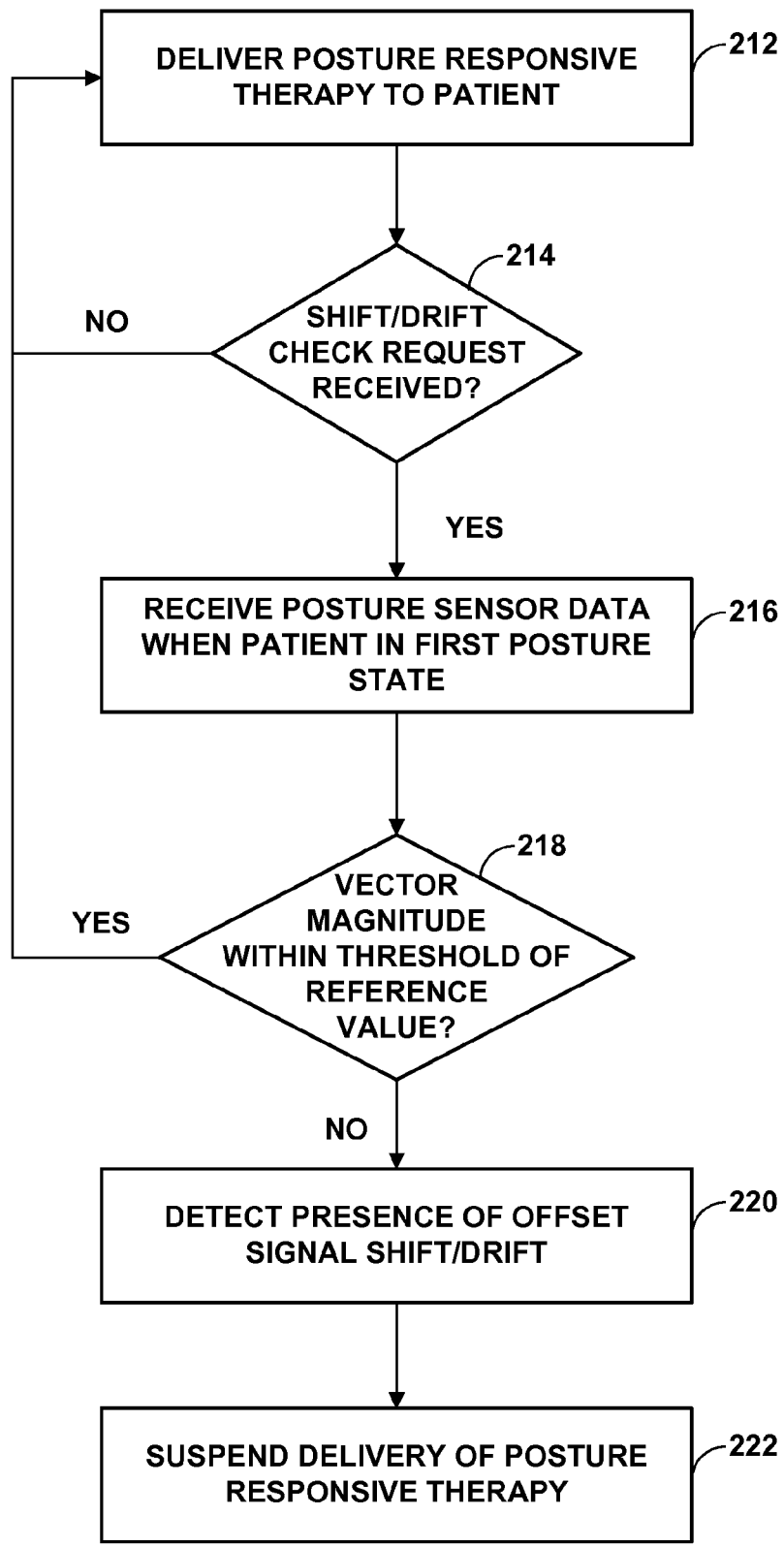
FIG. 14 is a flow diagram illustrating an example technique for suspending delivery of posture responsive therapy to a patient.

FIG. 14 is a flow diagram illustrating an example technique for suspending delivery of posture responsive therapy to patient 12 when processor 80 detects that offset shift/drift is present in the output of posture sensor 87. As shown, IMD 14 is active for delivery of posture responsive therapy to patient 12 (212). When IMD 14 is active for delivery of posture responsive therapy, processor 80 controls the therapy delivered to patient 12 according to the posture state of patient 12 detected by processor 80. As described above, processor 80 may detect the posture state of patient 12 based on the output of posture sensor 87.

At some point during the delivery of posture responsive therapy (212), processor 80 may receive a request to check the output of posture sensor 87 for the presence of offset shift/drift (214). For example, the request may be transmitted to processor 80 from external device 20 based on a user request communicated to external programmer 20 via user interface 106 (FIG. 6). In other examples, the request may correspond to one or more requests preprogrammed in memory 82 which are designed such that processor 80 automatically checks for the presence of offset shift/drift on a periodic basis. For example, processor 80 may be configured to check for the presence of offset shift/drift in the output of posture sensor 87 on a daily, weekly, and/or monthly basis.

As described above, to determine whether offset shift/drift is present in the output of posture sensor 87, processor 80 may receive posture sensor data that is based on the output of posture sensor 87 when patient occupies a first posture state (216). In the example of FIG. 14, the posture sensor data may include the magnitude of the posture vector determined from the posture sensor output using Equation 2 above. As describe above, this magnitude of the posture vector may then be compared to the magnitude defined by reference posture sensor data to determine whether or not the magnitude determined based on the "new" posture sensor output is within a threshold amount of the magnitude defined by the reference posture sensor data (218). Although the example of FIG. 14 is illustrated as comparing posture sensor data to reference posture sensor data for a single posture state, in other examples, processor 80 may perform substantially the same or similar comparison for each of a plurality of posture states. For example, as described above, processor 80 may perform substantially the same or similar comparison for at least three approximately orthogonal posture states.

If processor 80 determines that the magnitude of the posture vector for the first posture state is within the threshold value of the magnitude defined by the reference posture sensor data for the first posture state (which may be substantially the same or different for other posture states), processor 80 may determine that offset shift/drift is not present in the output of posture sensor and continue to deliver posture responsive therapy to patient 12. Conversely, if processor 80 determines that the magnitude of the posture vector for the first posture state is within the threshold value of the magnitude defined by the reference posture sensor data for the first posture state, processor 80 may detect that offset shift/drift is present in the output of posture sensor 220. Based on the detection of offset shift/drift, processor 80 may suspend the delivery of posture responsive therapy as a precaution. As will be described below, the posture responsive therapy may be suspended until an appropriate offset correction is applied to the posture detection algorithm to account for the detected offset shift/drift. In some examples, processor 80 may deliver some baseline stimulation preprogrammed to be delivered to patient 12 in instances in which offset shift/drift is detected.

In some cases, processor 80 may indicate the detection of the offset shift/drift to a user, e.g., via external programmer 20. The user may be given the choice whether or not to suspend delivery of the posture responsive therapy. In some instances, the user may decide whether or not to suspend the delivery of posture responsive therapy, e.g., in favor of some other predefined baseline therapy that is not responsive to the detect posture state of patient 12.

Figure 15:
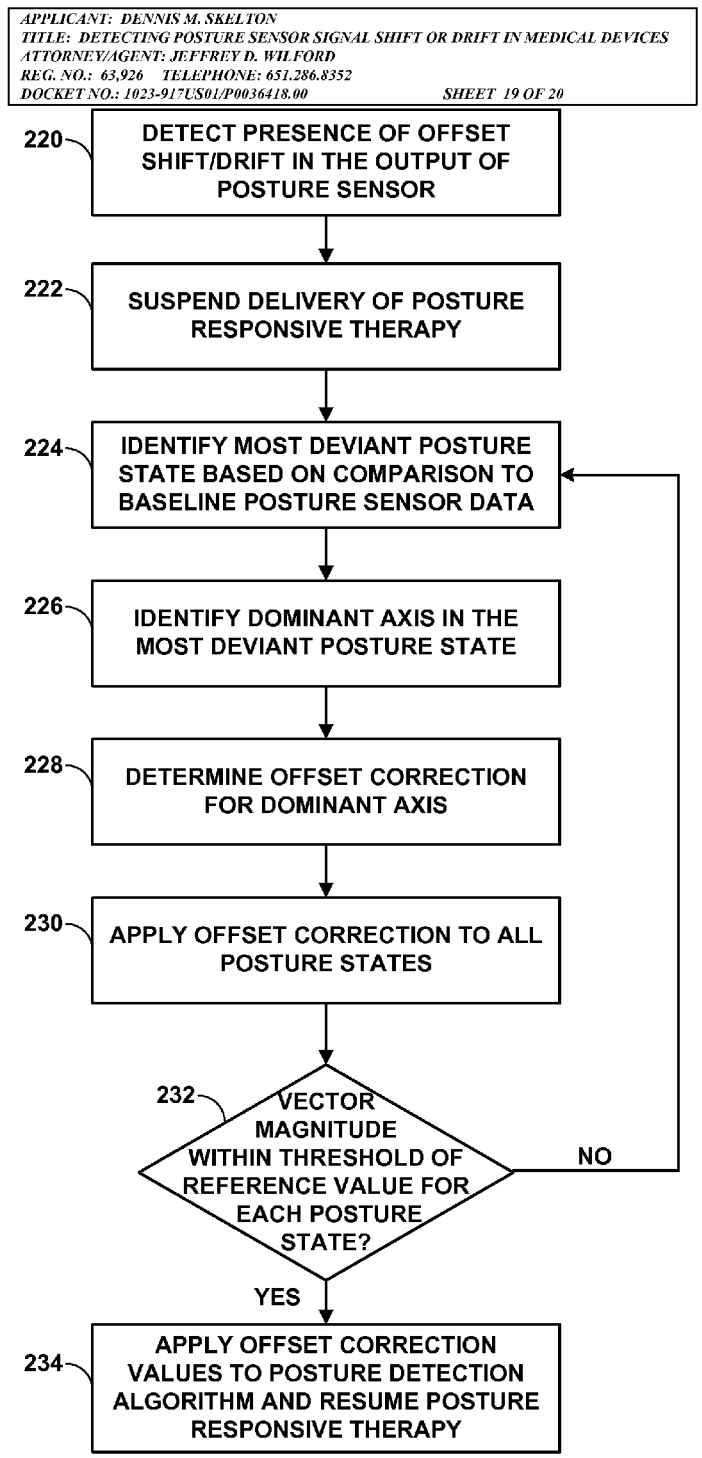
FIG. 15 is a flow diagram illustrating an example technique for determining an offset correction for application to an example posture state detection algorithm.

FIG. 15 is a flow diagram illustrating an example technique for determining an offset correction for application to a posture state detection algorithm. Processor 80 may utilize the posture state detection algorithm to analyze the output of posture sensor 87 to detect the posture state of patient 12. The offset correction determined by processor 80 may include offset correction values for one or more of the x, y, and z-axis signals that may be applied to the posture state detection algorithm used by processor. For example, as will be described below, a correction value may include one or more discrete values that are added to the output value for one or more of the signals generated along respective axes by the a posture detection algorithm when analyzing the postures sensor data to detect the posture state of patient 12.

As shown in FIG. 15, during the delivery of posture responsive therapy to patient 12, processor 80 may detect the presence of offset shift/drift in the output of posture sensor 87 (220). Processor 80 may detect the presence of the offset shift/drift using one or more of the example techniques described herein. For ease of illustration, the example technique of FIG. 15 is described for a scenario in which processor detects the presence of offset shift/drift by comparing the magnitude of a posture vector calculated using Equation 2 based on the signal output of patient 12 in one or more posture states to reference magnitude values associated each respective posture states representative of the output of postures sensor 87 when an offset shift/drift is not present. Again, the reference magnitude value associated with each posture state may be a magnitude value that is unique to a particular posture state or a single value that is applicable to multiple posture states, e.g., substantially all posture states of patient 12. However, other examples for determining the presence of offset shift/drift in the output of posture sensor 87 are contemplated.

Figure 16:
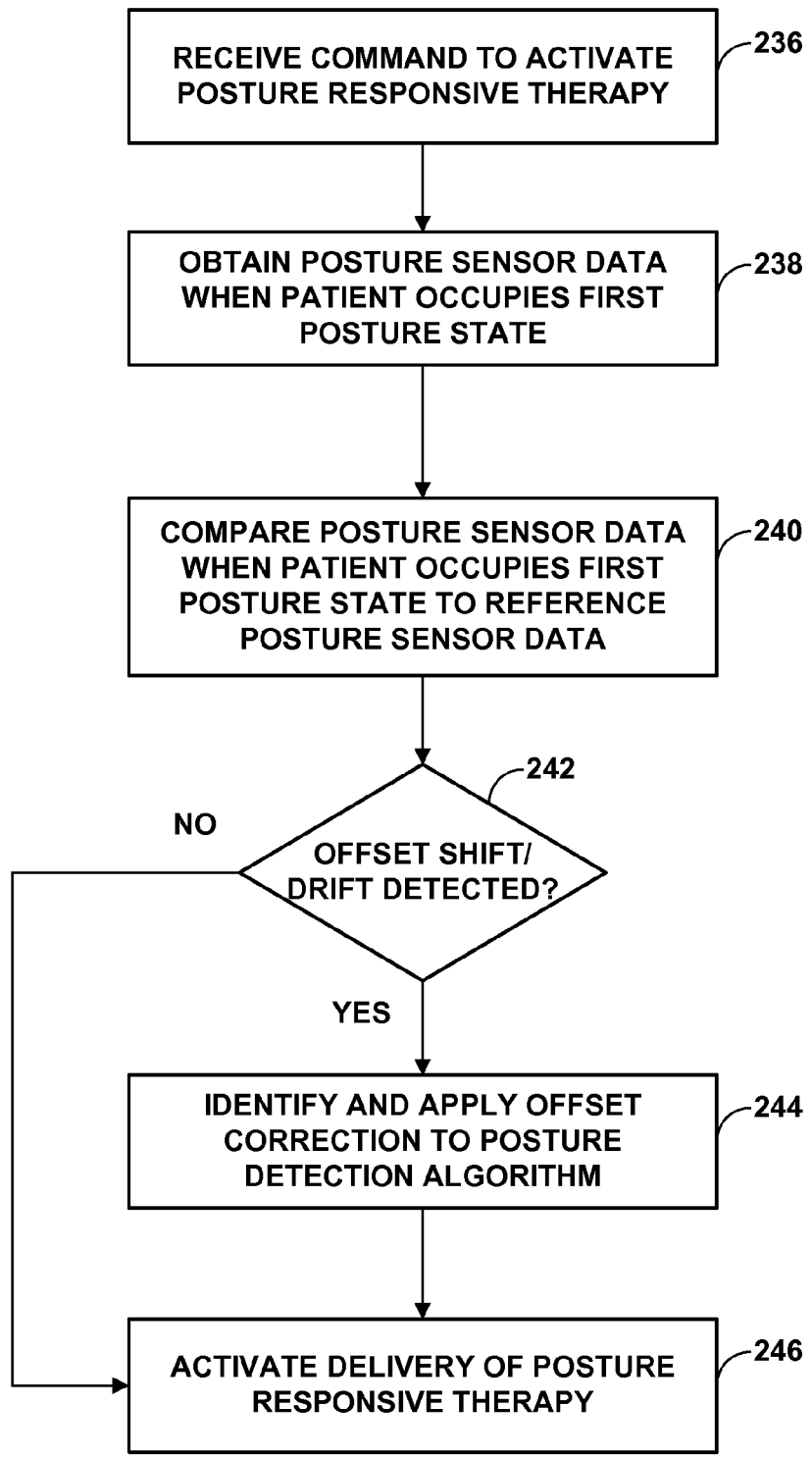
FIG. 16 is a flow diagram illustrating an example technique for activating a posture responsive therapy mode of an example IMD.

Upon detecting the offset shift/drift (220), processor 80 may suspend delivery of posture responsive therapy (222). In other examples, processor 80 may detect the presence of the offset shift/drift when IMD 14 is not actively delivering therapy to patient 12 according to the detected posture state of patient 12. In such examples, processor 80 does not suspend delivery of posture responsive therapy but may prevent the activation of posture responsive therapy until the offset shift/drift is corrected, e.g., via the application of one or more offset correction values. An example technique for preventing the activation of posture responsive therapy when an offset shift/drift is detected by processor 80 is illustrated in FIG. 16. In still other examples, processor 80 may continue to deliver posture responsive therapy to patient 12 while one or more offset correction values are determined by processor 80 to account for the offset shift/ drift present in the output of posture sensor 87.

After suspending delivery of posture responsive therapy to patient 12 (222), processor 80 may identify the most deviant posture state in view of the comparison for each posture state to reference posture sensor data (224). For ease of illustration, the example technique will be described for a scenario in which processor 80 uses posture sensor data for three posture states (upright posture state, lying back posture state, and lying right posture state) to determine an offset correction for the offset shift/drift present in the output of posture sensor 87. As described above, such posture states may be approximately orthogonal to each other in the three dimensional posture state space of the three-axis output of posture sensor 87. In some examples, the same three posture states may have been previously used by processor 80 to detect the presence of the offset shift/drift by way of comparison to reference posture sensor data. For each of the three posture states, processor 80 may determine the output value of each of the x, y, and z-axis, as well as a posture vector magnitude for each posture state determined using Equation 2. Based on this posture sensor data for each posture state, processor 80 may identify the most deviant posture state as the posture state with the greatest absolute difference between the magnitude of the posture vector and the reference magnitude value. For example, processor 80 may determine that the difference between magnitude of the posture vector for the upright posture state and the reference magnitude value for the upright posture is greater than that of the lying back and lying right posture states.

Processor 80 may then analyze the sensed x, y, and z-axis values for the upright posture state to determine the dominant axis for the most deviant posture state (226). For example, processor 80 may identify the most dominant axis as the axis with the largest output signal value. For example, assuming posture sensor data of [0,50,126.6] cG for the x, y, and z-axis, respectively, is generated by posture sensor 87 when patient occupies the upright posture state, processor 80 may identify the z-axis as the dominant axis of the posture sensor data for the upright posture state (226).

Once processor 80 identifies the dominant axis of the most deviant posture state (226), processor 80 may determine an offset correction value for the dominant axis. In the case of the z-axis being most dominant, processor 80 may employ Equation 3 to solve for the z-axis offset correction value, $Z_{corr}$;

$$Z_{corr} = +/- \sqrt{|V|_{init} - (V_x)^2 - (V_y)^2} - V_z \qquad (3)$$

where $V_x$ is the sensor output value along the x-axis, $V_y$ is the sensor output value along the y-axis, $V_z$ is the sensor output value along the z-axis, and $|V|_{init}$ is the reference magnitude value. As described above, such a reference value may be determined based on actual posture sensor data received from posture sensor 87, e.g., during an initial programming session after implant or determined prior to the implant of posture sensor 87, such as, during the manufacture of IMD 14.

If processor 80 determines that the x-axis is the most dominant axis, the processor 80 may employ Equation 4 to solve for the offset correction x-axis offset correction value, $X_{corr}$;

$$X_{corr} = +/- \sqrt{|V|_{init}^2 - (V_y)^2 - (V_z)^2} - V_x \qquad (4)$$

If processor 80 determines that the y-axis is the most dominant axis, the processor 80 may employ Equation 5 to solve for the offset correction y-axis offset correction value, $Y_{corr}$, $$Y_{corr} = +/- \sqrt{|V|_{init}^2 - (V_x)^2 - (V_z)^2} - V_y. \qquad (5)$$

After determining the offset correction value for the dominant axis (228), processor 80 may apply the offset correction value to the posture sensor data for each respective posture state (230) and determine if the magnitude of each posture vector for each posture state is within a threshold amount of the reference magnitude value associated with the respective posture state (232). For example, after applying the offset correction value for the z-axis determined for the upright posture state, processor 80 may determine the magnitude of the upright posture vector using x, y, and z-axis values of $[V_{s,\ upright},\ V_{y,\ upright},\ V_{z,\ upright} + Z_{corr,\ upright}]$ cGs, respectively, in Equation 2, where $V_{x,\ upright},\ V_{y,\ upright},$ and $V_{z,\ upright}$ are values of the x, y, and z-axis output signals, respectively, determined when patient 12 was in the upright posture state, and $Z_{corr,\ upright}$ is equal to the offset correction value determined for the z-axis (228). Similarly, processor 80 may determine the magnitude of the lying back posture vector using x, y, and z-axis values of $[V_{s,\ lying\ back},\ V_{y,\ lying\ back},\ V_{z,\ lying\ back} + Z_{corr,\ upright}]$ cGs, respectively, in Equation 2, where $V_{x,\ lying\ back},\ V_{y,\ lying\ back},$ and $V_{z,\ lying\ back}$ are values of the x, y, and z-axis output signals, respectively, determined when patient 12 was in the lying back posture state, and $Z_{corr,\ upright}$ is again equal to the offset correction value determined for the z-axis (228). For the lying front posture state, processor 80 may determine the magnitude of the lying right posture vector using x, y, and z-axis values of $[V_{s,\ lying\ right},\ V_{y,\ lying\ right},\ V_{z,\ lying\ right} + Z_{corr,\ upright}]$ cGs, respectively, in Equation 2, where $V_{x,\ lying\ right},\ V_{y,\ lying\ right},$ and $V_{z,\ lying\ right}$ are values of the x, y, and z-axis output signals, respectively, determined when patient 12 was in the lying right posture state, and $Z_{corr,\ upright}$ is equal to the offset correction value determined for the z-axis (228).

If processor 80 determines that the new magnitude of each posture vector determined with the offset correction applied to signal values as described above is within a threshold value of the reference magnitude value for each posture state, processor 80 may modify the posture detection algorithm stored in memory 82 to apply the offset correction value to the output signals generated by posture sensor 87 and resume the delivery of posture responsive therapy (234). Practically, such a modification may allow for the offset correction value determined for the z-axis to be applied every time for every signal thereafter along the z-axis to thereby compensate for the offset shift/drift present in the output of posture sensor 87 during normal operation of IMD 14, especially with regard to detection of the posture state of patient 12. In one example, an offset correction may be applied to the digital output used by the detection algorithm although the correction could be applied to the next sample of analog signal before the signal is converted from analog to digital. However, any suitable technique for applying an offset correction value to one or more of the x, y, and z-axis may be used.

The threshold value used by processor 80 may be substantially the same as the threshold value used to originally determine whether or not the comparison of posture sensor data generated by postures sensor 87 when patient actually occupies one or more posture states to reference posture sensor data is indicative of the presence of offset shift/drift in the posture sensor output, e.g., as described above with regard to FIG. 12. In some examples, the threshold value may be approximately equal to or greater than the variability inherent in the output signal(s) generated by posture sensor 87, e.g., due to varying gain errors on each axis. In some examples, a clinician or other authorized user may define the threshold value, e.g., based on previous experience with such offset shift/drift detection protocols.

Conversely, if processor 80 determines that the difference between the reference magnitude values for a posture state and the new magnitude of the posture vector for the posture states determined with the addition of the offset correction value is greater than the threshold value for any of the posture states, then processor 80 may perform another iteration of determining an offset correction value based on the new posture sensor data for each posture state.

To begin another iteration, processor 80 may again identify the most deviant posture state based on a comparison to the reference data (224). However, unlike the first iteration, processor 80 may analyze each posture state relative to the reference posture sensor data with the previously determined offset correction applied to the posture sensor data for each posture state. For example, processor 80 may determine which posture vector of the upright posture state, lying back posture state, and lying right posture state has the greatest magnitude using the new posture sensor data, i.e., the x, y, and z-axis value with the offset correction applied to the z-axis value. In other examples, processor 80 may indiscriminately select a new posture state or select any other posture state other than that posture state previously identified as the most deviant posture state (224). For illustrative purposes, processor 80 may select the lying back posture state as the most deviant posture state during the second iteration.

Once the next posture state is determined, processor 80 again may identify the most dominant axis for selected posture state (226). For example, processor 80 may again identify the most dominant axis as the axis with the largest output signal value but with the previously determined offset correction applied the output signal values. In some examples, after one or more iterations, processor 80 may identify a most dominant axis from only the axes that processor 80 has yet to determine an offset correction value. In the described example, processor 80 may determine which of the x-axis and y-axis has the greatest value and select that axis as that dominate axis since an offset correction value for the z-axis had already been determined by processor 80 in the first iteration.

Once the "dominant" axis is identified in the second iteration, processor 80 may determine an offset correction value for the axis, e.g., using whichever of Equations 3-5 is appropriate in view of the axis selected by processor 80 (228). After the offset correction is determined, processor 80 may apply the most recently determined offset correction value, as well as the offset correction value from the first iteration, to each the posture sensor data for each respective posture state (230) and determine if the magnitude of each posture vector for each posture state is within a threshold amount of the reference magnitude value associated with the respective posture state (232). As an illustration, if processor 80 determined an offset correction value for the y-axis during the second iteration, after applying both the z-axis and y-axis the offset corrections, the magnitude of the upright posture vector may be determined using x, y, and z-axis values of $[V_{x,\ upright},\ V_{y,\ upright} + Y_{corr,\ lying\ back},\ V_{z,\ upright} + Z_{corr,\ upright}]$ where $Y_{corr,\ lying\ back}$ is the offset correction value determined for the y-axis during the second iteration (228). Both the z-axis and y-axis offset values may applied in a similar fashion to the upright and lying right posture states when determining the magnitude of the posture vector for the respective posture state.

Processor 80 may continue to iteratively determine offset correction values until the offset correction values are such that, when applied to the posture sensor values for the respective posture states, the magnitude of the posture vectors for each posture state is within the threshold value of the respective reference magnitudes (232). Again, at that point, processor 80 may modify the posture detection algorithm stored in memory 82 to apply the offset correction value(s) to the output signals generated by posture sensor 87 and resume the delivery of posture responsive therapy to patient 12 (234). If processor 80 reaches an iteration in which an offset correction value has been applied to each axis of the posture sensor signal, processor 80 may override a previously determine offset correction value with a new correction value for that axis with the other offset correction values applied to the remaining axes. For example, if processor 80 determined offset corrections values for each of the x, y, and z-axis in the first three iterations in that order, processor 80 may determine a new offset correction value for the x-axis. However, processor 80 may determine the new offset correction for the x-axis using y and z-axis values with the previously determined correction values for each axis applied, rather than using the originally sensed values for the x and y-axis.

In some examples, processor 80 may limit the number of iterations for which a new offset correction value is determined using one or more suitable techniques. For example, processor 80 may employ one or more algorithms to determine whether or not the iterations are diverging or converging, as recursive algorithms may run forever without a check for divergence. Equation 6 is one example equation that may be used to check for convergence as the iterations progress, $$\lim_{n\to\infty} \frac{\sum S_n}{n} = r \tag{6}$$

where n is the iteration number, $S_n$ is equal to the maximum difference between the magnitude of the posture vector and reference magnitude value of the respective posture states for iteration n, and r is approximately equal to zero. When progressing through multiple iterations of the example process shown in FIG. 15, if processor 80 determines that:

$$\frac{\sum_{x=1}^{x=n-1} S_x}{n-1} < S_n, \tag{7}$$

then processor 80 may determine that the process is diverging from the goal of offset correction value(s) which result in the magnitude of posture vectors determined for each posture state, with the offset correction value(s) applied, to be within a threshold amount of the reference magnitude value for the respective posture state. In such examples, processor 80 may back up one or more iterations and calculate a different offset correction value for that previous iteration. On the first pass through, a given iteration the algorithm will use the most dominant axis of the most deviant posture. In some examples, on the second pass through a given iteration the algorithm may chose the second most dominant axis of the most deviant posture. In other examples, on the second pass through a given iteration the algorithm may chose the most dominant axis of the second most deviant posture. If the algorithm continues to diverge then the process may back up one or more iterations. On the third pass through a given iteration the algorithm may select the least dominant axis of the most divergent posture or alternatively may chose the most dominant axis on the least deviant posture. In this recursive manner, the algorithm could test all potential combinations of offset corrections applied to all combinations of axes.

Processor 80 may continue with the iterative process of FIG. 15 as long as the process is converging rather than diverging as determined per equation 7. In some examples, a maximum number of iterations may also be defined at which processor 80 may stop the iterative process even if the process is converging rather than diverging. Using Equation 7, processor 80 may employ a trailing average of the maximum difference between the magnitude of the posture vector and reference magnitude value for the previous iteration to allow the maximum difference, $S_n$, to increase or decrease slightly from the maximum difference determined from iteration n-1.

In some examples, upon detection of the presence of offset shift/drift in the output of posture sensor 87, one or more modifications may be made to the posture state reference data used by processor 80 to detect patient posture state, e.g., as described above with regard to FIGS. 8A-C, based on the output of posture sensor 87 to account for the offset shift/drift. For example, the angle used to define the posture zone or volume (e.g., posture cone) relative to a posture state reference vector may be adjusted to account for the offset shift/drift in the output of a sensor signal. In the scenario of FIGS. 9A-D, the angle of the lying back cone may be adjusted such that the upper boundary of the lying back cone is at approximately 60 degrees, as intended, by reducing the angle by approximately 11 degrees to account for the +40 cG offset shift present the output of the z-axis signal. However, such a modification may influence the location of the lower boundary of the lying back posture cone and effectively shrink the overall size of the posture cone. Moreover, to the extent that such an angle serves to define the posture space of for multiple posture states, e.g., such as a donut- or toroid-like volume that includes all of the lying postures, reducing such an angle to account for the influence of the offset shift/drift relative the lying back posture space may undesirably change the posture spaces defining other posture states, e.g., by reducing the upper boundary used to define the lying front posture space along the negative z-axis in the example of FIGS. 9A-D.

In some examples, such posture state reference data modification may be used in combination or as an alternative to the application of offset correction value(s) as described above. In some examples, such posture state reference data modification may be used to account offset shift/drift when the offset shift/drift is relatively minor, e.g., in cases in which the difference between current posture sensor data and reference posture sensor data is only slightly greater than a threshold amount, and the application of offset correction values may be used when the offset shift/drift that is present is more than minor. In some examples, such posture state reference data modifications may be used initially in one or more instances and then followed up with the application of one or more offset correction values at a later point in time, e.g., in the case when an offset drift continues to accumulate over time in a sensor signal.

FIG. 16 is a flow diagram illustrating a technique for activating a posture responsive therapy mode of IMD 14.

When IMD 14 is active for delivery of posture responsive therapy, processor 80 may control the therapy delivered to patient 12 according to the detected posture state of patient 12. When not activated for posture responsive therapy delivery, processor 80 may receive a command to activate posture responsive therapy delivery, e.g., as communicated from external programmer 20 to processor 80 of IMD 14 based on input received from patient 12 or other user (236). Upon receipt of such a command (236), processor 80 may first determine whether or not an offset shift/drift is present in the output of posture sensor 87, e.g., using one or more of the examples described herein. As shown, in one example, processor 80 may obtain recent posture sensor data based on the output of posture sensor 87 generated when patient 12 occupies a first posture state (238). Processor 80 may then compare the obtained posture sensor to reference posture sensor data associated with the first posture state (240) to determine if an offset shift/drift is present in the output of posture sensor 87 (242). The reference posture sensor data may or may not be unique to that of the first posture state. In some examples, as described above, processor 80 may analyze posture sensor data for a plurality of posture states rather than for only a first posture state.

If processor 80 determines that an offset shift/drift is not present in the output of posture sensor 87, then processor 80 may initiate the delivery of posture responsive therapy to patient 12 (246). Conversely, if processor 80 determines that an offset shift/drift is present in the output of posture sensor 87, then processor 80 may identify and apply offset correction value(s) to the posture detection algorithm to account for the offset shift/drift present in the output of posture sensor 87 (244). For example, processor 80 may utilize the example iterative process described with regard to FIG. 15 above to identify suitable offset correction value(s) and apply those correction value(s) to the posture detection algorithm used by processor 80 to detect the posture state of patient 12 based on the posture sensor data generated via posture sensor 87. In this manner, IMD 14 may be prevented from activating posture responsive therapy when offset shift/drift in present in the output of posture sensor 87 and not accounted for in the posture state detection algorithm.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
 receiving posture sensor data from a posture sensor;
 determining a posture state of a patient based on the posture sensor data;
 controlling delivery of therapy to the patient according to the determined posture state;
 comparing the posture sensor data from the posture sensor to reference posture sensor data; and
 detecting the presence of at least one of sensor signal drift or sensor signal shift for the posture sensor based at least in part on the comparison,
 and
 wherein at least one of the receiving, the determining, the comparing, and the detecting is performed via one or more processors.

2. The method of claim 1, wherein comparing the posture sensor data from the posture sensor to reference posture sensor data comprises determining one or more differences between the posture sensor data and the reference posture sensor data, and wherein detecting the presence of at least one of sensor signal drift or sensor signal shift for the posture sensor based at least in part on the comparison comprises detecting the presence of the at least one of sensor signal drift or sensor signal shift based on the one or more differences between the posture sensor data and the reference posture sensor data.

3. The method of claim 1, further comprising:
 determining an offset correction value based at least in part on the reference posture sensor data; and
 applying the offset correction value to a posture detection algorithm configured to detect patient posture state based at least in part on posture sensor data sensed via the posture sensor.

4. The method of claim 1, wherein the posture sensor data comprises first posture sensor data received from the posture sensor when a patient is in a first posture state, and the reference posture sensor data comprises first reference posture sensor data associated with the first posture state of the patient.

5. The method of claim 4, wherein the reference posture sensor data comprises baseline posture sensor data defined based on posture sensor data generated by the posture sensor when the patient previously occupied the first posture state.

6. The method of claim 4, further comprising:
 receiving second posture sensor data from the posture sensor when the patient is in a second posture state;
 comparing the second posture sensor data from the posture sensor to second reference posture sensor data associated with the second posture state; and
 wherein the presence of at least one of sensor signal drift or sensor signal shift for the posture sensor is detected based at least in part on the comparisons of the first posture sensor data and the second posture sensor data to the respective reference posture sensor data.

7. The method of claim 6, wherein the second reference posture sensor data associated with the second posture state is substantially the same as the first reference posture sensor data associated with the first posture state.

8. The method of claim 1, wherein the posture sensor comprises a multiple-axis accelerometer sensor, wherein the posture sensor data includes at least one of signal output values for respective axes or a magnitude vector determined based on signal output values from respective axes generated by the posture sensor.

9. The method of claim 1, further comprising generating an alert indicative of the presence of at least one of sensor signal drift or sensor signal shift for the posture sensor based at least in part on the comparison.

10. The method of claim 1, further comprising suspending delivery of the therapy when the at least one of sensor signal drift or sensor signal shift for the posture sensor is detected.

11. The method of claim 10, further comprising:
determining an offset correction value based on the reference posture sensor data;
applying the offset correction value to a posture detection algorithm configured to detect patient posture state based on sensed posture sensor data; and
resuming the suspended therapy after the offset correction value is applied to the posture detection algorithm.

12. The method of claim 1, further comprising receiving a command to initiate delivery of therapy, wherein the therapy is delivered according to the determined posture state of the patient, wherein the presence of at least one of sensor signal drift or sensor signal shift for the posture sensor is detected based on the receipt of the command to initiate delivery of the therapy.

13. The method of claim 1,
wherein the posture sensor comprises an accelerometer sensor including a first sensor output along a first axis, a second sensor output along a second axis, and a third sensor output along a third axis,
wherein the posture sensor data comprises first posture sensor data from the posture sensor when the patient occupies a first posture state, second posture sensor data from the posture sensor when the patient occupies a second posture state, and third posture sensor data from the posture sensor when the patient occupies a third posture state, and
wherein each of the first, second, and third posture sensor data includes respective posture vector magnitude values determined based on the first, second, and third sensor outputs when the patient occupies the respective posture states.

14. The method of claim 13, further comprising:
determining, upon detecting the presence of at least one of sensor signal drift or sensor signal shift, a first offset correction value for first posture sensor data of the first posture sensor data;
applying the first offset correction value to the second and third posture sensor data;
comparing the first, second, and third posture sensor data with the first offset correction applied to reference posture sensor data; and
determining whether to apply the first offset correction value to posture sensor data used to detect patient posture state based on the comparison of the first, second, and third posture sensor data with the first offset correction applied to reference posture sensor data.

15. The method of claim 13, wherein the first posture state, second posture state, and third posture state are approximately orthogonal to each other.

16. The method of claim 1, wherein the posture sensor data includes first posture sensor data and second posture state data, wherein determining a posture state of a patient based on the posture sensor data comprises determining a posture state of a patient based on the first posture sensor data from the posture sensor, and wherein comparing the posture sensor data from the posture sensor to reference posture sensor data comprises comparing the second posture sensor data from the posture sensor to the reference posture sensor data.

17. A medical device comprising:
a posture sensor configured to generate posture sensor data; and
at least one processor configured to receive the posture sensor data, determine a posture state of a patient based on the posture sensor data, control the delivery of therapy to a patient according to the determined posture state, compare the posture sensor data to reference posture sensor data, and detect at least one of sensor signal drift or sensor signal shift for the posture sensor based at least in part on the comparison.

18. The medical device of claim 17, wherein the at least one processor is configured to determine one or more differences between the posture sensor data and the reference posture sensor data, and detect the presence of the at least one of sensor signal drift or sensor signal shift based on the one or more differences between the posture sensor data and the reference posture sensor data.

19. The medical device of claim 17, wherein the at least one processor is configured to determine an offset correction value based at least in part on the reference posture sensor data; and apply the offset correction value to a posture detection algorithm configured to detect patient posture state based at least in part on posture sensor data sensed via the posture sensor.

20. The medical device of claim 17, wherein the posture sensor data comprises first posture sensor data received from the posture sensor when a patient is in a first posture state, and the reference posture sensor data comprises first reference posture sensor data associated with the first posture state of the patient.

21. The medical device of claim 20, wherein the reference posture sensor data comprises baseline posture sensor data defined based on posture sensor data generated by the posture sensor when the patient previously occupied the first posture state.

22. The medical device of claim 20, wherein the at least one processor is configured to receive second posture sensor data from the posture sensor when the patient is in a second posture state, compare the second posture sensor data from the posture sensor to second reference posture sensor data associated with the second posture state, and detect the presence of at least one of sensor signal drift or sensor signal shift for the posture sensor based at least in part on the comparisons of the first posture sensor data and the second posture sensor data to the respective reference posture sensor data.

23. The medical device of claim 22, wherein the second reference posture sensor data associated with the second posture state is substantially the same as the first reference posture sensor data associated with the first posture state.

24. The medical device of claim 17, wherein the posture sensor comprises a multiple-axis accelerometer sensor, wherein the posture sensor data includes at least one of signal output values for respective axes or a magnitude vector determined based on signal output values from respective axes generated by the posture sensor.

25. The medical device of claim 17, wherein the at least one processor is configured to generate an alert indicative of the presence of at least one of sensor signal drift or sensor signal shift for the posture sensor based at least in part on the detection.

26. The medical device of claim 17, wherein the at least one processor is configured to suspend the delivery of the therapy when the at least one of sensor signal drift or sensor signal shift for the posture sensor is detected.

27. The medical device of claim 26, wherein the at least one processor is configured to determine an offset correction value based on the reference posture sensor data, apply the offset correction value to a posture detection algorithm configured to detect patient posture state based on sensed posture sensor data; and resume the suspended therapy after the offset correction value is applied to the posture detection algorithm.

28. The medical device of claim 17, wherein the at least one processor is configured to receive a command to initiate delivery of therapy according to the determined posture state of the patient, and detect the presence of at least one of sensor signal drift or sensor signal shift for the posture sensor based on the receipt of the command to initiate delivery of the therapy.

29. The medical device of claim 17,
wherein the posture sensor comprises an accelerometer sensor including a first sensor output along a first axis, a second sensor output along a second axis, and a third sensor output along a third axis,
wherein the posture sensor data comprises first posture sensor data from the posture sensor when the patient occupies a first posture state, second posture sensor data from the posture sensor when the patient occupies a second posture state, and third posture sensor data from the posture sensor when the patient occupies a third posture state, and
wherein each of the first, second, and third posture sensor data includes respective posture vector magnitude values determined based on the first, second, and third sensor outputs when the patient occupies the respective posture states.

30. The medical device of claim 29, wherein the at least one processor is configured to determine, upon detecting the presence of at least one of sensor signal drift or sensor signal shift, a first offset correction value for first posture sensor data of the first posture sensor data, apply the first offset correction value to the second and third posture sensor data, compare the first, second, and third posture sensor data with the first offset correction applied to reference posture sensor data, and determine whether to apply the first offset correction value to posture sensor data used to detect patient posture state based on the comparison of the first, second, and third posture sensor data with the first offset correction applied to reference posture sensor data.

31. The medical device of claim 29, wherein the first posture state, second posture state, and third posture state are approximately orthogonal to each other.

32. The medical device of claim 17, wherein the posture sensor data includes first posture sensor data and second posture state data, wherein the at least one processor is configured to determine a posture state of a patient based on the first posture sensor data from the posture sensor, and compare the second posture sensor data from the posture sensor to the reference posture sensor data.

33. A non-transitory computer-readable storage medium comprising instructions for causing one or more processors to:
receive posture sensor data from a posture sensor;
determine a posture state of a patient based on the posture sensor data
control delivery of therapy to the patient according to the determined posture state
compare the posture sensor data from the posture sensor to reference posture sensor data; and
detect the presence of at least one of sensor signal drift or sensor signal shift for the posture sensor based at least in part on the comparison.

34. A system comprising:
means for receiving posture sensor data from a posture sensor;
means for determining a posture state of a patient based on the posture sensor data;
means for controlling delivery of therapy to the patient according to the determined posture state;
means for comparing the posture sensor data from the posture sensor to reference posture sensor data; and
means for detecting the presence of at least one of sensor signal drift or sensor signal shift for the posture sensor based at least in part on the comparison.

* * * * *